United States Patent [19]
Hagiya et al.

[11] Patent Number: 6,093,851
[45] Date of Patent: Jul. 25, 2000

[54] N-(α-ALKYLBENZYLIDENE)-α-PHENYLALKYLAMINE, ITS USE AND PROCESS FOR PRODUCING THE SAME AND PROCESS FOR PRODUCING INTERMEDIATE THEREFOR

[75] Inventors: Koji Hagiya, Takatsuki; Etsuko Harada, Ibaraki; Hideyuki Goto, Oita, all of Japan

[73] Assignee: Sumitomo Chemical Company, Ltd., Osaka, Japan

[21] Appl. No.: 09/134,354

[22] Filed: Aug. 14, 1998

Related U.S. Application Data

[62] Division of application No. 08/946,101, Oct. 7, 1997, which is a division of application No. 08/624,105, Mar. 29, 1996, Pat. No. 5,739,401.

[30] Foreign Application Priority Data

| Mar. 30, 1995 | [JP] | Japan | 7-073077 |
| Jul. 12, 1995 | [JP] | Japan | 7-176168 |
| Aug. 10, 1995 | [JP] | Japan | 7-204501 |
| Aug. 22, 1995 | [JP] | Japan | 7-213278 |
| Dec. 4, 1995 | [JP] | Japan | 7-315232 |
| Dec. 11, 1995 | [JP] | Japan | 7-321488 |

[51] Int. Cl.⁷ ........................ C07C 249/14; C07C 251/20
[52] U.S. Cl. ........................ 564/272; 564/248; 564/271
[58] Field of Search ........................ 564/248, 271, 564/272

[56] References Cited

U.S. PATENT DOCUMENTS 5,183,939  2/1993  Jansen et al. .

FOREIGN PATENT DOCUMENTS 0508307  10/1992  European Pat. Off. .
7-188120  7/1995  Japan .

OTHER PUBLICATIONS

Maslennikova et al, Zh. Org. Khim, 25(11), pp 2165–2170, 1989.
Itsuno et al, J. Chem. Soc. Perk. Trans. I, pp 2039–2044, 1985.
Arjona et al., "Origin of Mutarotation in Some N–Substituted Ketimines," J. Org. Chem. (1984), 49, 2624–2626.
Chemical Abstracts, vol. 113, No. 25, Abstract No. 23087lr (1990).
M.B. Eleveld et al., J. Org. Chem., vol. 51, pp. 3635–3641 (1986).
C. Lensink et al., Tetrahedron: Asymmetry, vol. 4, No. 2, pp. 215–222 (1993).
G. Bringmann et al., Tetrahedron Letters, vol. 30, No. 3, pp. 317–320 (1989).
A.D. Van Der Haest, Classical Resolutions: Design of Resolving Agents and Studies of Diastereomeric Salts; (Jul. 26, 1964).
A.W. Ingersoll et al., J. Am. Chem. Soc., 58, 1808 (1936).
P.V. Atanas et al., Synthetic Communications, 23(12), 1707–1719 (1993).
R.D. Guthrie et al., J. Am. Chem. Soc., 95:9, (May 2, 1973).
Acta chimica Scandinavica, 47, 1046–1049 (1993).
Organic Syntheses, vol. II, 503 (1943).
Organic Reactions, vol. V, 301–325, p. 321 (1949).
Chemical Abstracts, vol. 93, 167778s (1980).
Acta Polon, Pharm. XXXVI, Nr.2 (1979).

*Primary Examiner*—Shailendra Kumar
*Attorney, Agent, or Firm*—Birch, Stewart, Kolasch & Birch, LLP

[57] ABSTRACT

There is disclosed an N-(α-alkylbenzylidene)-α-phenylalkylarmine represented by the general formula (1):

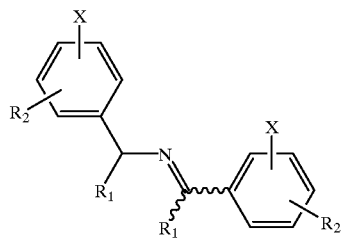

(1)

wherein $R^1$ represents a lower alkyl group, $R^2$ represents a hydrogen atom, a halogen atom, a lower alkyl group or a lower alkoxy group and X represents a halogen atom or a lower alkoxy group, its use and a process for producing the same and processes for producing intermediates therefor.

12 Claims, No Drawings

N-(α-ALKYLBENZYLIDENE)-α-PHENYLALKYLAMINE, ITS USE AND PROCESS FOR PRODUCING THE SAME AND PROCESS FOR PRODUCING INTERMEDIATE THEREFOR

This application is a divisional of application Ser. No. 08/946,101, filed on Oct. 7, 1997, which is a divisional of allowed application Ser. No. 08/624,105, filed on Mar. 29, 1996, U.S. Pat. No. 5,739,401 the entire contents of which are hereby incorporated by reference.

FIELD OF THE INVENTION

The present invention relates to N-(α-alkylbenzylidene)-α-phenylalkylamine, its use, a process for producing the same and a process for producing intermediates therefor.

RELATED PRIOR ART

Optically active α-phenylalkylamines are useful compounds which are intermediates for agricultural chemicals and pharmaceuticals, such as phenylalkylcarbamate type pesticides and aralkylamine type calcium antagonists (for example, see JP-A 63-238054, JP-A 2-76846, JP-A 2-11550). As a process for producing optically active 1-(2', 4'-dichlorophenyl)ethylamine, there has been known a process by optically resolving its racemate using N-formylphenylalanine as a resolving agent (JP-A 2-306942). As a process for production of optically active 1-(3-methoxyphenyl)ethylamine, there has been known a process by optically resolving its racemate using malic acid or the like as a resolving agent (JP-A 58-41847).

It has been desired that the undesirable antipode which is left after separation of useful optically active compound is effectively used, for example, that the undesirable compound is converted to its racemate by racemization to reuse the compound.

As a process for producing racemate of α-arylalkylamines by racemization of optically active compounds thereof, there have been known a process for producing racemate of α-phenylethylamines by a treatment with sodium naphthalene (JP-A 50-49235), a process for producing racemate of α-naphthylethylamines by a treatment with sodium hydride (JP-A54-5967), a process for producing racemate of α-phenylethylamine by a treatment with sodium carried on alumina (JP-A 50-50328) and the like.

However, when the above known processes were applied, for example, to optically active α-halogen-substituted phenylalkylaminess, there arises a problem that racemization reaction does not proceed at all. In addition, when applied to optically active α-alkoxy-substituted phenylalkylamines, there arises a problem that racemization reaction does not proceed at all depending upon the kind of the amines and that a large amount of catalyst is required and sufficient yield can not be obtained even in the case of the amines where racemization reaction proceeds.

On the other hand, as a process for producing racemate of α-halogen-substituted phenylalkylamines by racemization of optically active α-halogen-substituted phenylalkylamines, there has also been known a process for producing racemate of 1-(4-chlorophenyl)ethylamine by a treatment with alkali metal alkoxide in dimethyl sulfoxide. However, when this process was applied, for example, to other optically active α-halogen- or α-alkoxy-substituted phenylalkylamines, there arises a problem that racemization reaction does not proceed at all depending upon the kind of the amines and that a large amount of catalyst is required and the sufficient yield can not be obtained even in the case of the amines where the reaction proceeds.

OBJECTS OF THE INVENTION

A main object of the present invention is to provide a useful N-(α-alkyibenzylidene)-α-phenylalkylamine and a process for producing the same.

Another object of the present invention is to provide a process for producing useful intermediates therefor.

These objects as well as other objects and advantages of the present invention will become apparent from the following description.

SUMMARY OF THE INVENTION

Under these circumstances, the present inventors studied processes for producing α-phenylalkylamines by racemization of optically active compounds. As a result of intensive studies, they discovered that compounds obtainable by condensing optically active α-phenylalkylamines with phenyl alkyl ketones are easily racemized by a treatment with alkali metal alkoxides in a specific solvent and that the racemates thereof can be easily converted to α-phenylalkylamines. By the discoveries and further studies, the present invention had been accomplished.

That is, the present invention relates to an N-(α-alkylbenzylidene)-α-phenylalkylamine represented by formula (1):

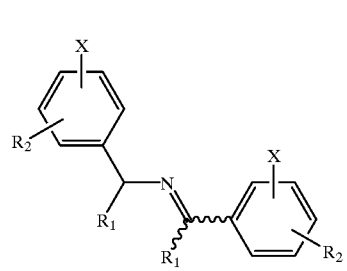

(1)

wherein the $R^1$ substituents may be the same or different and represent a lower alkyl group, the $R^2$ substituents may be the same or different and represent a hydrogen atom, a halogen atom, a lower alkyl group or a lower alkoxy group, and X substituents may be the same or different and represent a halogen atom or a lower alkoxy group, as well as its use, a process for producing the amines and a process for producing intermediates therefor.

DETAILED DESCRIPTION

The present invention will be described in detail.

As used herein, "an optically active isomer of a compound" means the R isomer in pure form or substantially free from the S isomer, S isomer in pure form or substantially free from the R isomer, or a mixture of the R isomer and the S isomer which contains an excess of either the R isomer or the S isomer, except for optically active mandelic acid below.

An optically active isomer of an N-(α-alkylbenzylidene)-α-phenylalkylamine (1) in the present invention can be prepared by condensing an optically active α-phenylalkylamine represented by formula (2):

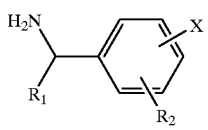

(2)

wherein R¹, R² and X are as defined above, with a phenyl alkyl ketone represented by formula (3):

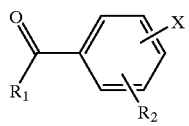

(3)

wherein R¹, R² and X are as defined above. Preferably, in formula (1), the R¹ substituents are the same, the R² substituents are the same and the X substituents are the same. Preferably, the R² and X substituents are attached to the phenyl moiety at the same position.

The phenyl alkyl ketone of formula (2) are commercially available or may be produced by known processes or by analogy with known processes.

R¹ in formula (1) and (2) is typically a lower alkyl groups having 1 to 5 carbon atoms, preferably 1 to 4 carbon atoms. Typically, R¹ is a methyl group, ethyl group, n-propyl group, isopropyl group, n-butyl group, isobutyl group, sec-butyl group, pentyl group, and the like. Methyl is preferred.

Examples of R² are hydrogen atom; halogen atoms such as fluoro atom, chloro atom and bromo atom; lower alkyl groups having 1 to 4 carbon atoms, such as methyl group, ethyl group, n-propyl group, isopropyl group, n-butyl group, isobutyl group, sec-butyl group and the like, and lower alkoxy groups having 1 to 3 carbon atoms, such as methoxy group, ethoxy group, n-propoxy group, isopropoxy group and the like.

Examples of X are the same halogen atoms and lower alkoxy groups as those described in R².

Specific examples of optically active isomers of α-phenylalkylamine (2) are optically active isomers of 1-(2'-chlorophenyl)ethylamine, 1-(3'-chlorophenyl)ethylamine, 1-(4'-chlorophenyl)ethylamine, 1-(2',3'-dichlorophenyl) ethylamine, 1-(2',4'-dichlorophenyl)ethylamine, 1-(2',5'-dichlorophenyl)ethylamine, 1-(2',6'-dichlorophenyl) ethylamine ,1-(3',4'-dichlorophenyl)ethylamine, 1-(3',5'-dichlorophenyl)ethylamine, 1-(4'-bromophenyl)ethylamine, 1-(2',4'-dibromophenyl)ethylamine, 1-(3'-bromophenyl) ethylamine, 1-(3',4'-dibromophenyl)ethylamine, 1-(2'-methoxyphenyl)ethylamine, 1-(3'-methoxyphenyl) ethylamine, 1-(4'-methoxyphenyl)ethylamine, 1-(2',3'-dimethoxyphenyl)ethylamine, 1-(2',4'-dimethoxyphenyl) ethylamine, 1-(3',4'-dimethoxyphenyl)ethylamine, 1-(3',5'-dimethoxyphenyl)ethylamine, 1-(2'-methyl-4'-chlorophenyl)ethylamine, 1-(3'-methyl-4'-chlorophenyl) ethylamine, 1-(2'-bromo-4'-ethylphenyl)ethylamine, 1-(3'-chloro-4'-ethylphenyl)ethylamine, 1-(2'-methoxy-4'-bromophenyl)ethylamine, 1-(3'-methoxy-4'-chlorophenyl) ethylamine, 1-(2'-bromo-4'-ethoxyphenyl)ethylamine, 1-(3'-chloro-4'-ethoxyphenyl)ethylamine, 1-(2',4'-dichlorophenyl)isobutylamine, 1-(3',4'-dichlorophenyl) isobutylamine, 1-(3'-methoxyphenyl)isobutylamine, 1-(3',4'-dimethoxyphenyl)isobutylamine, 1-(3',4'-dichlorophenyl) propylamine, 1-(2'-fluorophenyl)ethylamine, 1-(3'-fluorophenyl)ethylamine and 1-(3'-methoxyphenyl) propylamine.

Examples of R¹ in phenyl alkyl ketone (3), formula (4), formula (5) and formula (6) are the same as the examples given for R¹ in α-phenylalkylamine (2). Methyl is preferable.

Examples of R² in phenyl alkyl ketone (3), formula (4), formula (5) and formula (6) are the same as the examples given for R² in α-phenylalkylamine (2).

Examples of X in formula (3), formula (4), formula (5) and formula (6) are the same as the examples given for X in α-phenylalkylamine (2).

Specific examples of phenyl alkyl ketone (3) are 2'-chloroacetophenone, 3'-chloroacetophenone, 4'-chloroacetophenone, 2',3'-dichloroacetophenone, 2',4'-dichloroacetophenone, 2',5'-dichloroacetophenone, 2',6'-dichloroacetophenone, 3',4'-dichloroacetophenone, 3',5'-dichloroacetophenone, 3'-bromoacetophenone, 4'-bromoacetophenone, 2',4'-dibromoacetophenone, 3',4'-dibromoacetophenone, 2'-methyl-4'-chloroacetophenone, 3'-methyl-4'-chloroacetophenone, 2'-bromo-4'-ethylacetophenone, 3'-methoxy-4'-ethylacetophenone, 2'-methoxy-4'-bromoacetophenone, 3'-methoxy-4'-chloroacetophenone, 2,-bromo-4'-ethoxyacetophenone, 3'-chloro-4'-ethoxyacetophenone, 2'-methoxy-4'-bromoacetophenone, 2',4'-dichlorophenyl isopropyl ketone, 3',4'-dichlorophenyl isopropyl ketone, 3'-methoxyphenyl isopropyl ketone, 3',4'-dimethoxyphenyl isopropyl ketone, 3',4'-dichlorophenyl ethyl ketone, 2'-chlorophenyl ethyl ketone, 3'-chlorophenyl ethyl ketone, 4'-chlorophenyl ethyl ketone, 2'-chlorophenyl i-propyl ketone, 3'-chlorophenyl i-propyl ketone, 4'-chlorophenyl i-propyl ketone, 2-chlorophenyl n-propyl ketone, 3'-chlorophenyl pentyl ketone, 2'-methoxyacetophenone, 3'-methoxyacetophenone, 2',3'-dimethoxyacetophenone, 2',4'-dimethoxyacetophenone, 3',4'-dimethoxyacetophenone, 3',5'-dimethoxyacetophenone, 2'-fluoroacetophenone, 3'-fluoroacetophenone, 4'-fluoroacetophenone, 3'-chloro-4'-fluoroacetophenone and 3-methoxyphenyl ethyl ketone. Usually, phenyl alkyl ketone (3) have the same kind and position of substituents R¹, R² and X as do the α-phenylalkylamine (2).

Optically active isomer of N-(α-alkylbenzylidene)-α-phenylalkylamine (1) can be obtained by condensing optically active isomer of α-phenylalkylamine (2) with phenyl alkyl ketone (3) according to the known process, for example, disclosed in J. Org. Chem., (1984), 49, 2624–2626. In the condensation reaction, phenyl alkyl ketone (3) is usually used at an amount of 0.5 to 2 mole, preferably 0.95 to 1.05 mole, per one mole of optically active isomer of α-phenylalkylamine (2).

The condensation reaction is usually carried out in the presence of a catalyst and a solvent. Alternatively, the reaction may be carried out without a solvent. When a solvent is used, solvents may be used as long as they do not ED affect adversely on the reaction. Examples of the solvent are aromatic hydrocarbons, such as toluene, benzene, xylene, chlorobenzene and the like; ethers such as dioxane, methyl t-butyl ether and the like; aliphatic hydrocarbons such as hexane, heptane and the like; and halogenated hydrocarbons such as dichloroethane, chloroform and the like. The reaction is preferably carried out while water produced by the condensation is removed from the reaction system.

The amount of the solvent to be used is usually 0 to 20 parts by weight, preferably 3 to 10 parts by weight, per one part by weight of optically active isomer of α-phenylalkylamine (2).

Examples of the catalyst are Lewis acids such as zinc chloride, zinc bromide, zinc fluoride, titanium tetrachloride, boron trifluoride, boron tribromide, phosphorus trichloride, magnesium bromide, iron chloride, aluminium chloride, tin tetrachloride, titanium alkoxide, copper (II) triflate and the like; sulfonic acids such as benzenesulfonic acid, p-toluenesulfonic acid, sulfonic ion-exchange resin and the like; and heteropolyacids such as 12-tungsto(IV)phosphoric acid, 12-tungsto(IV)silicic acid and the like.

Among them, zinc chloride, titanium alkoxide, titanium tetrachloride, boron trifluoride and p-toluenesulfonic acid are preferably used. More preferably, zinc chloride and titanium alkoxide are used.

The amount of the catalyst to be used is usually 0.001 to 0.1 mole, preferably 0.005 to 0.05 mole per one mole of optically active isomer of α-phenylalkylamine (2).

Reaction temperature is usually from about 70 to 180° C. The reaction is preferably carried out while water produced by the condensation is removed from the reaction system.

A reaction time is usually about 1 to 20 hours.

The resulting optically active isomer of N-(α-alkylbenzylidene)- α-phenylalkylamine (1) may be used as it is in the next step after the catalyst is removed from the reaction mixture. Alternatively, fractions having low boiling point may be removed, for example, by distillation or the like. Alternatively, the optically active isomer of compound (1) may be further purified by distillation, recrystallization, various chromatographies or the like after separation.

Thus, optically active isomer of N-(α-alkylbenzylidene)-α-phenylalkylamine (1) are obtained. Examples thereof are optically active isomers of N-(α-methyl-2'-chlorobenzylidene)-α-(2'-chlorophenyl)ethylamine, N-(α-methyl-3'-chlorobenzylidene)-α-(3'-chlorophenyl)ethylamine, N-(α-methyl-4'-chlorobenzylidene)-α-(4'-chlorophenyl)ethylamine, N-(α-ethyl-2'-chlorobenzylidene)-α-(2'-chlorophenyl)propy lamine, N-(α-ethyl-3'-chlorobenzylidene)-α-(3'-chlorophenyl) propylamine, N-(α-ethyl-4'-chlorobenzylidene)-α-(4'-chlorophenyl)propylamine, N-(α-n-propyl-2'-chlorobenzylidene)-α-(2'-chlorophenyl)-n-butylamine, N-(α-n-propyl-3'-chlorobenzylidene)-α-(3 -chlorophenyl)-n-butylamune, N-(α-n-propyl-4'-chlorobenzylidene)-α-(4'-chlorophenyl)-n-butylamine, N- (α-methyl-2',3'-dichlorobenzylidene)-α-(2',3'-dichlorophenyl)ethylamine, N-(α-methyl-2',4'-dichlorobenzylidene)-α-(2',4'-dichlorophenyl)ethylamine, N-(α-methyl-2',5'-dichlorobenzylidene)-α-(2,5'-dichlorophenyl)ethylamine, N-(α-methyl-2',6'-dichlorobenzylidene)-α-(2',6'-dichlorophenyl)ethylamine, N-(α-methyl-3',4'-dichlorobenzylidene)-α-(3',4'-dichlorophenyl)ethylamine, N-(α-methyl-3',5'-dichlorobenzylidene)-α-(3',5'-dichlorophenyl)ethylamine, N-(α-methyl-2',5'-dichlorobenzylidene)-α-(2',5'-dichlorophenyl)ethylamine, N-(α-ethyl-2',4'-dichlorobenzylidene)-α-(2',4'-dichlarophenyl)propylamine, N-(α-ethyl-3',4'-dichlorobenzylidene)-α-(3',4'-di chlorophenyl)propylamine, N-(α-ethyl-2',5'-dichlorobenzylidene)-α-(2',5'-dichlorophenyl)propylamine, N-(α-methyl-4'-bromobenzylidene)-α-(4'-bromophenyl)ethylamine, N-(α-ethyl-2'-bromobenzylidene)-α-(2'-bromophenyl)propylamine, N-(α-ethyl-3'-bromobenzylidene)-α-(3'-bromophenyl) propylamine, N-(α-ethyl-4'-bromophenyl)-α-(4'-bromopheny 1)propylamine, N-(α-methyl-2',4'-dibromobenzylidene)-α-(2',4'-dibromophenyl)ethylamine, N-(α-ethyl-2',4'-dibromobenzylidene)-α-(2',4'-dibromophenyl)propylamine, N-(α-methyl-2'-chloro-4'-methylbenzylidene)-α-(2'-chloro-4'-methylphenyl)ethylamine, N-(α-ethyl-3'-chloro-4'-methylbenzylidene)-α-(3'-chloro-4'-methylphenyl) propylamine, N-(α-methyl-2'-chloro-4'-methoxybenzylidene)-α-(2'-chloro-4'-methoxyphenyl) ethylamine, N-(α-ethyl-3'-chloro-4'-methoxybenzylidene)-α-(3'-chloro-4'-methoxyphenyl)propylamine N-(α-isopropyl-2',4'-dichlorobenzylidene)-α-(2',4'-dichlorophenyl)isobutylamine, N-(α-isopropyl-3',4'-dichlorobenzylidene)-α-(3',4'-dichlorophenyl) isobutylamine, N-(α-ethyl-3'-methoxybenzylidene)-α-(3'-methoxyphenyl)propylamine, N-(α-ethyl-3',4'-dimethoxybenzylidene)-α-(3',4'-dimethoxyphenyl) propylamine, N-(α-methyl-2'-methoxybenzylidene)-α-(2'-methoxyphenyl)ethylamine, N- (α-methyl-3'-methoxybenzylidene)-α-(3'-methoxyphenyl)ethylamine, N-(α-methyl-2',3'-dimethoxybenzylidene)-α-(2',3'-dimethoxyphenyl)ethylamine, N-(α-methyl-2',4'-dimethoxybenzylidene)-α-(2',440 -dimethoxyphenyl) ethylamine, N-(α-methyl-3',4'-dimethoxybenzylidene)-α-(3',4'-dimethoxyphenyl)ethylamine, N-(α-methyl-3',5'-dimethoxybenzylidene)-α-(3',5'-dimethoxyphenyl) ethylamine, N-(α-methyl-2'-fluorobenzylidene)-α-(2'-fluorophenyl)ethylamine and N-(α-methyl-3'-fluorobenzylidene)-α-(3'-fluorophenyl)ethylamine.

The optically-active isomer of N-(α-alkylbenzylidene)-α-phenylalkylamine (1) can be racemized by treatment with an alkali metal alkoxide in the presence of dimethyl sulfoxide.

N-(α-alkylbenzylidene)-α-phenylalkylamine (1) wherein $R^2$ and/or X is lower alkoxy group such as methoxy group are particularly effective in the racemization compared with conventional processes.

Examples of appropriate alkali metal alkoxide are salts of tertiary alkoxides with alkali metals such as potassium t-butoxide, sodium t-butoxide, potassium t-amyloxide, sodium t-amyloxide and the like.

The amount of the alkali metal alkoxide to be used is usually 0.01 to 2 mole, preferably 0.03 to 0.2 mole, per one mole of N-(α-alkylbenzylidene)-α-phenylalkylamine (1).

The amount of dimethyl sulfoxide to be used is usually 0.1 to 10 mole, preferably 0.5 to 5 mole, per one mole of N-(α-alkylbenzylidene)-α-phenylalkylamine (1). Dimethyl sulfoxide may be, of course, used as a solvent at a large amount.

Racemization reaction is usually carried out in the presence of a solvent.

The solvents may be used as long as they do not affect adversely on the reaction. Examples of the solvent are aromatic hydrocarbons such as toluene, benzene, xylene, chlorobenzene and the like; ethers such as diethyl ether, methyl t-butyl ether, dioxane and the like; aliphatic hydrocarbons such as hexane, heptane and the like; and dimethyl sulfoxide.

The amount of the solvent varies depending upon the kind of the solvent used and is usually 0.3 to 100 parts by weight, preferably 0.5 to 10 parts by weight, per one part by weight of N-(α-alkylbenzylidene)-α-phenylalkylamine (1).

Reaction temperature and reaction time vary depending upon the kind and the amount of alkali metal alkoxide and the like. Reaction temperature is usually from 0° C. to boiling point of the solvent used, preferably from 0 to 100° C., more preferably from 10 to 80° C., particularly preferably from 10 to 50° C. Reaction time is usually about 1 to 48 hours.

The progression of the reaction can be monitored by polarimetry, i.e. by collecting a portion of the reaction mixture and measuring the angle by which it rotates polarised light. Alternatively, it is possible to analyse the composition of the reaction mixture by high performance liquid chromatography using an chiral column after hydrolysis.

The resulting racemate of N-(α-alkylbenzylidene)-α-phenylalkylamine (1) may be usually used as it is in the next step after dimethyl sulfoxide, alkali metal alkoxide or decomposition products thereof are removed from the reaction mixture by washing with an aqueous solution containing an inorganic salt such as sodium chloride. Alternatively, the compound (1) may be separated by distilling off fractions having low boiling point or the like. Alternatively, the compound (1) may be further purified by distillation, recrystallization, various chromatographies or the like after separation.

Racemate of N-(α-alkylbenzylidene)-α-phenylalkylamine (1) can be converted to racemate of α-phenylalkylamine (2) and phenyl alkyl ketone (3) by hydrolysis.

The hydrolysis is carried out, for example, in the presence of an acid such as dilute aqueous hydrochloric acid or dilute aqueous sulfuric acid optionally in the presence of a solvent.

The amount of the acid to be used is usually 1 to 10 equivalents, preferably 1.05 to 1.5 equivalents of the racemate of N-(α-alkylbenzylidene)-(x-phenylalkylamine (1).

The amount of Water including the one in the acid is usually from 1 to 1000 mole, preferably 20 to 100 mole, per one mole of racemate of N-(α-alkylbenzylidene)-α-phenylalkylamine (1).

When a solvent is used, the amount thereof is usually 0.1 to 5 parts by weight per one part by weight of racemate of N-(ac-alkylbenzylidene)-α-phenylalkylamine (1).

The solvents may be used as long as they do not affect adversely on the reaction. Examples of the solvent are alcohol such as methanol, ethanol and the like; aliphatic hydrocarbons such as hexane, heptane and the like; halogenated hydrocarbons such as dichloroethane, chloroform and the like; esters such as ethyl acetate and the like; ethers such as dioxane, diethyl ether and the like; and aromatic hydrocarbons such as toluene, benzene, xylene, chlorobenzene and the like.

Reaction temperature and reaction time vary depending upon the kind and amount of the solvent used. The temperature is usually from 0° C. to boiling point of the solvent, preferably from about 30 to 70° C. The reaction time is usually 10 minutes to 5 hours.

Water-soluble acid salt of racemate of α-phenylalkylamine (2), and phenyl alkyl ketone (3) are formed by the hydrolysis. When the reaction is carried out without a solvent, racemate of α-phenylaklylamines (2) can be taken out by adding a water-insoluble solvent to the reaction mixture to extract and separate phenyl alkyl ketone (3) into oil layer, making the aqueous layer alkaline with an aqueous alkali solution such as an aqueous sodium hydroxide solution, extracting the alkaline aqueous layer with a water-insoluble solvent, and concentrating the resulting organic layer under reduced pressure.

When hydrolysis is carried out using an aqueous solvent such as alcohols or the like, after the alcohol is distilled off, the above treatment may be carried out. When a water-insoluble solvent is used, the same treatment as that described above may be carried out except that layers of the reaction mixture are separated as it is to extract and separate phenyl alkyl ketone (3) into the organic layer.

Alternatively, racemate of α-phenylalkylamine (2) may be taken out by steam-distilling the reaction mixture to remove phenyl alkyl ketone (3), adjusting aqueous layer to alkaline with an aqueous alkali solution such as aqueous sodium hydroxide solution, extracting with a water-insoluble solvent, and concentrating the resulting organic layer under reduced pressure.

Alternatively, the reaction mixture is adjusted to alkaline using an aqueous alkali solution such as aqueous sodium hydroxide solution, followed by extraction with a water-insoluble solvent to obtain a mixture of phenyl alkyl ketone (3) and racemate of α-phenylalkylamine (2), which may be subjected to conventional separation method such as column chromatography or the like to separate both compounds.

The separated and recovered phenyl alkyl ketone (3) can be recycled as raw materials.

Racemate of α-phenylalkylamine (2) can be optically resolved according to a method, for example, by J. Chem. Soc., (B) 1971, 2418, Bull. Chem. Soc. Jpn., 66, 3414 (1993), or J. Am. Chem. Soc., 105, 1584 (1983), to obtain optically active isomer of α-phenylalkylamine (2).

The optical resolution of 1-(3,4-dichlorophenyl)ethylamine, 1-(2,4-dichlorophenyl)ethylamine, 1-(2,3-dichlorophenyl)ethylamine, 1-(2-fluorophenyl)ethylamine, 1-(2-chlorophenyl)ethylamine, 1-(3,4-dimethoxyphenyl)ethylamine and the like (hereinafter, referred to as substituted amines (2)) using optically active mandelic acid is explained below.

As optically active mandelic acid, either S- or R-mandelic acid is used depending upon which isomer of optically active substituted amines (2) is required.

The amount of the optically active mandelic acid used is usually about 0.1 to 1.2 moles, preferably about 0.3 to 1 mole per one mole of the racemate of the substituted amines (2).

This reaction is usually carried out in an organic solvent. Examples of the solvent used are alcohols such as methanol, ethanol, n-propanol and the like; ketone such as acetone, methyl isobutyl ketone and the like; esters such as ethyl acetate and the like; ethers such as methyl t-butyl ether, dioxane, diethyl ether and the like; aromatic hydrocarbons such as toluene, xylene, chlorobenzene and the like; nitriles such as acetonitrile and the like; and a mixture of two or more of these. The solvent may contain water.

The amount of the solvent to be used varies depending upon the kind of solvent and that of substituted amines (2) and is usually 2 to 100 parts by weight, preferably 2 to 10 parts by weight, per one part by weight of racemate of the substituted amines (2).

Upon the optical resolution, after racemate of the substituted amines (2) and optically active mandelic acid are reacted in the above solvent to form diastereomer salts or pre-prepared diastereomer salts are dissolved in the above solvent, one of diastereomers is precipitated while settling or stirring the solution, and if necessary, cooling or condensing. The temperature is usually from −20° C. to boiling point of the solvent.

Thereafter, the precipitated salts are separated. If necessary, the resulting salt may be recrystallized. Then, the salt is decomposed using an alkali and the resulting oil or crystals is/are separated or extracted with an organic solvent to obtain the optically active substituted amines (2).

The remaining aqueous layer from which the oil or crystals has/have been separated or extracted may be made acidic with an acid, followed by extraction with an organic solvent to recover optically active mandelic acid.

On the other hand, the similar procedures to those described above may be applied to the mother liquor after one of diastereomers have been separated, to recover optically active isomer of substituted amines (2) having different absolute configuration and optically active mandelic acid.

Examples of alkali used for decomposing diastereomer salts are hydroxides, carbonates and bicarbonates of alkali metal such as sodium hydroxide, potassium hydroxide, sodium carbonate, sodium bicarbonate and the like. The amount of the alkali is usually 1 to 5 moles per one mole of the salt.

Examples of the solvent used for extracting optical isomers of the substituted amines (2) produced by salt decomposition are esters such as ethyl acetate and the like; ethers such as methyl t-butyl ether, tetrahydrofuran, diethyl ether and the like; and aromatic hydrocarbons such as toluene, xylener chlorobenzene and the like. The amount of the solvent is usually 0.1 to 5 parts by weight per one part by weight of the salt.

Examples of the acid used for recovering optically active mandelic acid are mineral acids such as hydrochloric acid, sulfuric acid, phosphoric acid and the like. The acid is used so that pH of the aqueous layer becomes 0.5 to 2. In this case, a salt such as sodium chloride or the like may be added thereto. The amount of the salt such as sodium chloride is usually about 0.1 to 0.2 part by weight per one part by weight of the aqueous layer.

Examples of the solvent used for extracting optically active mandelic acid are ethers such as methyl t-butyl ether and the like, esters such as ethyl acetate and the like, and alcohols which form separate layer to water, such as n-butanol and the like. The amount of the solvent is about 0.1 to 10 parts by weight per one part by weight of the aqueous layer.

α-Phenylalkylamine (2) can be prepared by a method heating a mixture of phenyl alkyl ketone (3), ammonium formate and formic acid according to J. Am. Chem. Soc., 58, 1808 (1936) or J. Am. Chem. Soc., 60, 919 (1938), or a method by heating a mixture of phenyl alkyl ketone (3) and formamide to obtain phenylalkylformamide represented by formula (4):

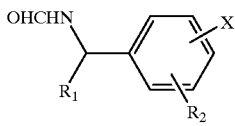

(4)

wherein $R^1$ and $R^2$ are as defined above, and hydrolyzing the phenylalkylformamide (4). Alternatively, a α-phenylalkylamine (2) may be prepared by reacting phenyl alkyl ketone (3) with ammonia and hydrogen in the presence of Raney-nickel catalyst deactivated by a sulfur compound at a pressure of 120 atmospheric pressures as described in JP-A 2-73042.

However, since the yield of phenylalkylformamide (4) is low in the method described in J. Am. Chem. Soc., 58, 1808 (1936) or J. Am. Chem. Soc., 60, 919 (1938), the yield of α-phenylalkylamine (2) is consequently insufficient. In addition, in the method of JP-A 2-73042, there is not only a facility problem caused under a high pressure condition during the method, but also a problem that by-products such as alcohol, resulting from direct reduction of the phenyl alkyl ketone (3), are produced. Therefore, an improved method has been desired.

Thus, the present inventors discovered that an α-phenylalkylamine of formula (2) can be obtained at a high yield by adding a corresponding ketone and formic acid concurrently to formamide and/or ammonium formate. Such a process can be applied to not only α-phenylalkylamine (2) but also a wider variety of compounds than the α-phenylalkylamine (2).

The method is explained below.

N-formylamine represented by formula (4'):

$R^3R^4CH\text{-}NH\text{-}CHO$ (4')

wherein $R^3$ represents lower alkyl group, unsubstituted or substituted aryl group or unsubstituted or substituted aralkyl group and $R^4$ represents unsubstituted or substituted aryl group or unsubstituted or substituted aralkyl group, can be obtained by adding ketone represented by formula (3'):

$R^3R^4C\!=\!O$ (3')

wherein $R^3$ and $R^4$ are as defined above, and formic acid concurrently to formamide and/or ammonium formate.

$R^3$ represents a lower alkyl group, an optionally substituted aryl group or an optionally substituted aralkyl group. Examples of lower alkyl group are alkyl groups having 1 to 7 carbon atoms, such as methyl group, ethyl group, n-propyl group, i-propyl group, n-butyl group, i-butyl group, sec-butyl group, t-butyl group, pentyl group, and the like.

Examples of optionally substituted aryl group are unsubstituted aryl groups having 6 to 13 carbon atoms such as phenyl group, naphthyl group and the like; aryl groups, such as phenyl group, naphthyl group and the like, having 7 to 14 carbon atoms and having 1 to 3 substituents. Examples of the substituent are halogen atoms such as fluorine atom, chlorine atom, bromine atom, and the like; nitro group; the same lower alkyl groups as those described above; lower haloalkyl groups having 1 to 7 carbon atoms such as difluoromethyl group, trifluoromethyl group, and the like; lower alkoxy groups having 1 to 7 carbon atoms such as methoxy group, ethoxy group, n-propoxy group, i-propoxy group, n-butoxy group, i-butoxy group, sec-butoxy group, t-butoxy group, pentoxy group, and the like; lower haloalkoxy groups having 1 to 7 carbon atoms such as difluoromethoxy group, trifluoromethoxy group, and the like; lower aryloxy groups having 6 to 13 carbon atoms such as phenyloxy group, and the like; aralkyloxy groups having 7 to 14 carbon atoms such as benzyloxy group, and the like; and methylenedioxy group.

Examples of optionally substituted aralkyl group are unsubstituted aralkyl groups having 7 to 14 carbon atoms such as benzyl group, naphthylmethyl group and the like, and aralkyl groups, such as benzyl group, naphthylmethyl group and the like, having 7 to 14 carbon atoms and having 1 to 3 substituents. Typically, the alkyl moiety is a said lower alkyl group. Examples of the substituent are halogen atoms such as fluorine, chlorine, bromine, and the like; nitro group; the same lower alkyl groups as those described above; lower haloalkyl groups having 1 to 7 carbon atoms such as difluoromethyl group, trifluoromethyl group, and the like; lower alkoxy groups having 1 to 7 carbon atoms such as methoxy group, ethoxy group, n-propoxy group, i-propoxy group, n-butoxy group, i-butoxy group, sec-butoxy group, t-butoxy group, pentoxy group, and the like; lower haloalkoxy groups having 1 to 7 carbon atoms such as difluoromethoxy group, trifluoromethoxy group, and the like.

Examples of optionally substituted aryl group and optionally substituted aralkyl group in $R^4$ are the same as those described in $R^3$.

When the above phenyl alkyl ketone (3) are used as the ketone (3'), α-phenylalkylformamide (4) can be obtained.

Typical examples of the ketone (3') are, in addition to the compounds described in the above phenyl alkyl ketone (3), acetophenone, 2'-nitroacetophenone, 3'-nitroacetophenone, 4'-nitroacetophenone, 4'-methoxyacetophenone, 2'-trifluoromethylacetophenone, 3'-trifluoromethylacetophenone, 4'-trifluoromethylacetophenone, 2'-trifluoromethylacetophenone, 3'-trifluoromethoxyacetophenone, 4'-trifluoromethoxyacetophenone, butyrophenone, 2'-methylacetophenone, 2'-chloro-4'-trifluoromethylacetophenone, 2'-nitrophenyl i-butyl ketone, 4'-methylphenyl propyl ketone, benzophenone, 4-chlorobenzophenone, benzyl methyl ketone, 2'-chlorobenzyl methyl ketone, 3'-methylbenzyl methyl ketone, 2'-methoxybenzyl methyl ketone, 3'-methoxybenzyl methyl ketone, 4'-methoxybenzyl methyl ketone, 3',4'-dichlorobenzyl methyl ketone, 3',4'-dimethoxybenzyl methyl ketone, 3'-bromo-4'-methoxybenzyl methyl ketone, 3'-trifluoromethylbenzyl methyl ketone, benzyl phenyl ketone, 4'-methylbenzyl phenyl ketone, 4t-methoxybenzyl phenyl ketone, 3',4'-dimethoxybenzyl phenyl ketone, 3'-benzyloxyacetophenone, 3',4'-methylenedioxyacetophenone, 3',4'-methylenedioxybenzyl methyl ketone, 1'-acetonaphthone, 2'-acetonaphthone, and the like.

Commercially available formamide or ammonium formate may be used, or formamide or ammonium formate prepared by reaction of formic acid and aqueous ammonia or ammonia gas may also be used. The amount thereof is usually 1 to 10 moles, preferably 2 to 4 moles in terms of nitrogen, per one mole of ketone (3').

The amount of formic acid to be used is usually 0.1 to 10 moles, preferably 0.5 to 5 moles, more preferably 0.7 to 4 moles, per one mole of ketone (3'). Formic acid containing water, ammonium formate and the like can be used.

This reaction is characterized in that ketone (3') and formic acid are added concurrently to formamide and/or ammonium formate. The ketone (3') and formic acid may be added separately, or a mixture thereof may be added to formamide and/or ammonium formate.

Reaction temperature is usually from about 150 to 200° C., preferably from about 155 to 175° C. The ketone (3') and formic acid are usually added over about 0.5 to 10 hours. After the addition, stirring may usually be continued for 1 to 10 hours.

It is preferred that ammonia produced from the reaction is captured with formic acid in an apparatus such as an ammonia recovering tower and recycled to the reaction and/or used in the next reaction as ammonium formate. By-product ammonia can be utilized effectively by the ammonia recycle, and as the result, the substantial amount of formamide and/or ammonium formate to be used may be reduced.

In That case, the piping from a reaction vessel to an ammonia recovering tower are preferably lagged at 80 to 120° C., whereby adhesion of ammonium carbonate to the wall can be prevented to improve the recovery rate of ammonia.

After the reaction, N-formylamine (4') thus obtained may be isolated by distilling off fractions having low boiling point from the reaction mixture.

If necessary, N-formylamine (4') may be purified by distillation, recrystallization or the like. The recovered low boiling point fractions contain formamide and the like, which may be reused.

The resultant N-formylamine (4') may be hydrolyzed in a solvent or without a solvent in the presence of dilute aqueous hydrochloric acid or sulfuric acid to obtain a corresponding amine represented by formula (2'):

$$R^3R^4CHNH_2 \quad (2')$$

wherein $R^3$ and $R^4$ are as defined above.

Of course, in the case where the raw material ketone (3') used in the preparation of N-formylamine (4') is a phenyl alkyl ketone of formula (3), the resulting amine (2') is an α-phenylalkylamine (2).

The amount of the acid used for this hydrolysis is usually 1 to 10 equivalents, preferably 1.05 to 2 equivalents of N-formylamine (4').

The amount of water including the water in the dilute aqueous acid is usually 1 to 1000 moles, preferably 20 to 100 moles, per one mole of N-formylamine (4').

When a solvent is used, the amount thereof is usually 1 to 1000 moles, preferably 20 to 100 moles, per one mole of N-formylamine (4').

Any solvent may be used as long as it does not adversely affect on the reaction. Examples thereof are alcohols such as methanol, ethanol, and the like; esters such as ethyl acetate, and the like; ethers such as dioxane, diethyl ether, and the like; aromatic hydrocarbons such as toluene, xylene, chlorobenzene, and the like.

Reaction temperature and reaction time vary depending upon the kind and amount of the solvent used. The temperature is usually from 0° C. to boiling point of the solvent, preferably from about 30 to 100° C. The reaction time is usually from 10 minutes to 5 hours.

Water-soluble salt of the corresponding amine and acetic acid, and formic acid are formed by the hydrolysis. When the hydrolysis is carried out without a solvent, amines can be isolated by adding a water-insoluble solvent to the reaction mixture to extract and separate the neutral by-products into the organic layer, adjusting the aqueous layer to alkaline with an aqueous alkaline solution such as aqueous sodium hydroxide solution or the like, extracting the alkaline aqueous layer with a water-insoluble solvent to obtain the organic layer, and then the organic layer is concentrated under reduced pressure.

When the hydrolysis is carried out using a water-soluble solvent such as alcohols or the like, after the alcohol is distilled off, the above treatment may be carried out. When a water-insoluble solvent is used, the layer of reaction mixture are separated as it is to extract the neutral by-products into the organic layer and the same treatment as that described above may be carried out.

In addition, crude amines (2') thus obtained may be treated by the conventional separation means such as distillation, column chromatography or the like to isolate the amine (2').

α-Phenylalkylamine of formula (2) may also be obtained by catalytic hydrogenation of oxime acetate represented by formula (5):

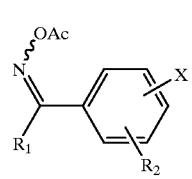

(5)

wherein $R^1$, $R^2$ and X are as defined above, in an organic carboxylic acid in the presence of platinum catalyst. This process has such characteristics that an α-phenylalkylamine (2) can be effectively prepared at a high yield at a low pressure almost without by-product alcohols. This process is particularly advantageous when X is a chlorine atom and $R^2$ is it hydrogen atom or chlorine atom in the α-phenylalkylamine (2) since the production of by-products derived from dechlorination is inhibited.

This process is explained below.

Examples of X, $R^1$ and $R^2$ in oxime acetate (5) are the is same as those described above. In this reaction, it is preferred that X is chlorine atom and $R^2$ is chlorine atom or hydrogen atom.

Examples of the oxime acetate (5) are oxime acetate of the above phenyl alkyl ketone (3).

Oxime acetate (5) can be easily prepared by reacting the corresponding phenyl alkyl ketone (3) with a acid salt of hydroxylamine in the same manner as that in Organic Synthesis Collective Vol. 6,278, to obtain ketoxime represented by formula (6):

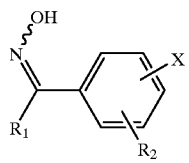

(6)

wherein $R^1$, $R^2$ and X are as defined above, and esterifying using an acylating agent.

Examples of the acid salt of hydroxylamine are mineral acid salts such as hydrochloride, sulfate, phosphate of hydroxylamine. The amount of the salt to be used is usually 1 to 1.1 moles per one mole of phenyl alkyl ketone (3).

The reaction is usually carried out in a solvent. Examples of the solvent are a mixture of water and water-miscible alcohol such as mixture of water and methanol, a mixture of water and ethanol and the like, a mixture of water and a water-immiscible solvent such as a mixture of water with hexane, heptane, toluene, methylene chloride, dichloroethane, methyl t-butyl ether and the like- In the latter case, the reaction can be proceeded smoothly by using a phase transfer catalyst. The amount of the solvent to be used is 1 to 10 parts by weight per one part by weight of phenyl alkyl ketone (3).

Although the reaction proceeds at room temperature, it can be promoted by heating at a temperature in a range from 50 to 60° C. As the reaction proceeds, a mineral acid is released. The mineral acid is neutralized with an aqueous alkali solution such as aqueous sodium hydroxide solution, aqueous sodium carbonate solution, aqueous ammonia or the like during or after the reaction.

The resulting ketoxime (6) may be isolated by distilling the solvent off to obtain the crystals which are washed with water and dried in the case where the ketoxime (6) are obtained as crystals, or by separating the organic layer, followed by washing with water and removal of the solvent by distillation in the case where the resulting ketoxime (6) are dissolved in the organic layer.

Examples of the acylating agent used for esterifying ketoxime (6) are acetic anhydride, and acetic halides such as acetic chloride, acetic bromide and the like. The acylating agent is usually used at the amount of 1 to 1.1 moles per one mole of the ketoxime (6). When oxime acetate (5) are used for catalytic-hydrogenation as they are without isolation, the amount is preferably 1 to 1.05 moles, thereby production of by-product amide may be inhibited.

The reaction is usually carried out in a solvent. Examples of the solvent are carboxylic acids such as formic acid, acetic acid, propionic acid and the like, hexane, heptane, toluene, methylene chloride, dichloroethane, methyl t-butyl ether and the like. The amount of the solvent to be used is usually 1 to 10 parts by weight per one part by weight of ketoxime (6). Reaction temperature is usually from about 50° C. to boiling point of the solvent, preferably from about 50° C. to 120° C.

After the reaction, oxime acetate (5) can be isolated by distilling off the solvent and the acylating agent remained.

When an carboxylic acid is used as a solvent, the reaction mixture may directly be catalytic-hydrogenated without isolation.

A platinum catalyst used for catalytic-hydrogenating oxime acetate (5) is not limited and may usually used the one carried on a carrier such as carbon, silica gel, alumina or the like.

The platinum catalyst is usually used at an amount of 0.05 to 1% by weight, preferably 0.1 to 0.2% by weight in term of platinum, to the oxime acetate (5).

Examples of the carboxylic acid used for catalytic-hydrogenating the oxime acetate (5) are lower carboxylic acids having 1 to 3 carbon atoms such as formic acid, acetic acid, propionic acid and the like. Among them, acetic acid is preferred.

The carboxylic acid is used at an amount of 1 to 100 parts by weight, preferably 5 to 10 parts by weight, per one part by weight of the oxime acetate (5).

The catalytic-hydrogenating reaction-is usually carried out at a temperature in a range from about 10 to 50° C., preferably from about 20 to 40° C. The reaction is preferably carried out at a temperature of not higher than 50° C. since production of by-products such as dimer, ketones and the like tends to increase when the temperature exceeds 50° C.

Since the reaction rate is decreased and production of the by-products such as dimer, amide and the like tend to increase at below 5 kg/cm$^2$·G, the hydrogen pressure is usually not lower than 5 kg/cm$^2$·G, preferably in a range from 5 to 50 kg/cm$^2$·G. The reaction proceeds sufficiently even at a range from 5 to 30 kg/cm$^2$·G.

After completion of the reaction, α-phenylalkylamine (2) thus formed can be isolated by for example, separating the catalyst, distilling the carboxylic acid off, neutralizing with an aqueous base solution such as aqueous sodium hydroxide solution or the like, extracting with an organic solvent and distilling the organic solvent off.

If necessary, the α-phenylalkylamine (2) may be purified by distillation, recrystallization or the like.

In addition, the separated and recovered catalyst can be reused.

According to the N-(α-alkylbenzylidene)-α-phenylalkylamine (1) of the present invention, a useless optically active isomer of α-phenylalkylamine (2) can easily and effectively converted to a racemate of α-phenylalkylamine (2) which is reusable as a raw material for a useful optically active compound under a mild condition.

In addition, according to the present invention, N-(α-alkylbenzylidene)-α-phenylalkylamine (1) and intermediates therefor can effectively be produced.

The following Examples and Comparative Examples illustrate the present invention in-detail but are not to be construed to limit the scope thereof.

EXAMPLE 1

155.1 g of ammonium formate was placed in a reaction vessel equipped with a Dean-Stark separating apparatus, the compound was heated to 155 ° C., and 98.5 g of acetophenone and 49.6 g of 76% formic acid were added thereto, respectively, for 3 hours under stirring, followed by stirring at 160° C. for 3 hours. During the reaction, the distillate was separated and acetophenone layer (upper layer) was returned to the reaction vessel and these procedures were repeated at interval.

After cooled to room temperature, low boiling point fraction was distilled off from the reaction mixture under reduced pressure to obtain 116.1 g of crude N-formyl-1-phenylethylamine.

Purity of the crude N-formyl-1-phenylethylamine was 87.5% as analyzed by gas chromatography.

EXAMPLE 2

In the same manner as in Example 1 except that 139.6 g of 1'-acetonaphthone was used in place of acetophenone, the reaction and post treatment were carried out to obtain 164.5 g of crude N-formyl-1-naphthylethylamine; the purity: 82.3%.

EXAMPLE 3

In the same manner as in Example 1 except that 110.7 g of formamide was used in place of ammonium formate and 126.7 g of 4'-chloroacetophenone was used in place of acetophenone, the reaction and post treatment were carried out to obtain 150 g of crude N-formyl-1-(4-chlorophenyl) ethylamine; the purity: 87.4%.

EXAMPLE 4

In the same manner as in Example 1 except that 155 g of 2',4'-dichloroacetophenone was used in place of acetophenone, the reaction and post treatment were carried out to obtain 170.8 g of crude N-formyl-1-(2,4-dichlorophenyl)ethylamine; the purity: 78.9%.

EXAMPLE 5

An ammonia absorbing tower and a reaction vessel were connected and 206 g of ammonium formate was placed in the reaction vessel. 233 g of 76% formic acid was placed in a pot of the ammonia absorbing tower, and was circulated in the tower at a speed of 20 g/min. while the connecting part between the absorbing tower and the reaction vessel was lagged so as to maintain at 80° C.

The reaction vessel was heated to 155° C. with stirring, 2',4'-dichloroacetophenone and a pot solution of the ammonia absorbing tower were concurrently added to the vessel at 0.86 g/min. and at 0.48 g/min. respectively over 3 hours, followed by stirring at a temperature in a range from 155 to 160° C. for 7 hours. During the reaction, formic acid was continued to be circulated.

After the reaction, the low boiling point fraction was distilled off under reduced pressure to obtain 162.2 g of crude N-formyl-1-(2,4-dichlorophenyl)ethylamine; the purity: 86%.

The fraction obtained by distilling the low boiling point fraction was 137.9 g, which was measured by gas chromatography and found to contain 69.8% of formamide, 12.9% of formic acid and 1.7% of 2',4'-dichloroacetophenone.

The pot solution of the ammonia absorbing tower after the reaction was 229.2 g, and was found to contain 4.7% of formamide, 36.7% of formic acid, 0.2% of ammonium formate and 1.7% of 2',4'-dichloroacetophenone.

EXAMPLE 6

A mixture of 56.8 g of 27% aqueous ammonia, 137 g of distillate recovered in Example 5 and 113 g of the pot solution of the ammonia absorbing tower was distilled under reduced pressure to distill off 166 g of water.

This concentrate was placed in the reaction vessel, and the same procedures as those in Example 5 was repeated except that 130 g of 90% formic acid and 116 g of the pot solution of the ammonia absorbing tower recovered in Example 5 were placed in the pot of the ammonia absorbing tower.

165.4 g of crude N-formyl-1-(2,4-dichlorophenyl) ethylamine was obtained; the purity: 83.7%.

The distillate obtained by distilled off low boiling point fraction was 112.5 g, which was found to contain 80.1% of formamide, 15.7% of formic acid and 1.2% of 2',4'-dichloroacetophenone.

In addition, the pot solution of the ammonia absorbing tower was 265 g, which was found to contain 6% of formamide, 31.5% of formic acid, 0.2% of ammonium formate and 3% of 2'1,4-dichloroacetophenone.

EXAMPLE 7

In the same manner as in Example 1 except that 123.2 g of 2'-methoxyacetophenone was used in place of acetophenone, the reaction and post treatment were carried out to obtain 143.7 g of crude N-formyl-1-(2-methoxyphenyl)ethylamine; the purity: 90%.

EXAMPLE 8

In the same manner as in Example 1 except that 123.2 g of 3'-methoxyacetophenone was used in place of acetophenone, the reaction and post treatment were carried out to obtain 130.4 g of crude N-formyl-1-(3-methoxyphenyl)ethylamine; the purity: 93%.

EXAMPLE 9

In the same manner as in Example 5 except that 405 q of ammonium formate was placed in the reaction vessel, 569 g of 76% formic acid was placed in the pot of the ammonia absorbing tower, 3'-benzyloxyacetophenone and the pot solution of the ammonia absorbing tower were added to the vessel at 2.54 g/min. and 3–6 g/min. respectively over 3 hours in place of 2',4'-dichloroacetophenone at 0.86 g/min. and the pot solution of the ammonia absorbing tower at 0.48 g/min, and the stirring time after addition was 10 hours in place of 7 hours, the reaction and post treatment were carried out to obtain 497 g of crude N-formyl-1-(3-benzyloxyphenyl)ethylamine (the purity: 97.8%) in place of 2',4'-dichloroacetophenone at 0.86 g/min. and the pot solution of the ammonia absorbing tower at 0.48 g/min.

EXAMPLE 10

In the same manner as in Example 1 except that 135.5 g of 3'-nitroacetophenone was used in place of acetophenone, the reaction and post treatment were carried out to obtain 139.8 g of crude N-formyl-1-(3-nitrophenyl)ethylamine; the purity: 91.1%

EXAMPLE 11

In the same manner as in Example 1 except that 113.3 g of 2'-fluoroacetophenone was used in place of acetophenone, the reaction and post treatment were carried out to obtain 125.8 g of crude N-formyl-1-(2-fluorophenyl)ethylamine; the purity: 87.2%.

EXAMPLE 12

In the same manner as in Example 1 except that 147.9 g of 3',4'-dimethoxyacetophenone was used in place of acetophenone, the reaction and post treatment were carried out to obtain 156.8 g of crude N-formyl-1-(3,4-dimethoxyphenyl)ethylamine; the purity: 96.2%.

EXAMPLE 13

In the same manner as in Example 1 except that 155.1 g of 3'-trifluoromethylacetophenone was used in place of acetophenone, the reaction and post treatment were carried out to obtain 166.5 g of crude N-formyl-1-(3-trifluoromethylphenyl)ethylamine; the purity: 85.7%.

EXAMPLE 14

In the same manner as in Example 1 except that 159.1 g of 3',4'-dimethoxybenzyl methyl ketone was used in place of acetophenone, 413.7 g of ammonium formate was used, and 41.9 g of 90% formic acid was used in place of 76% formic acid, the reaction and post treatment were carried out to obtain 165.6 g of crude N-formyl-2-(3,4-dimethoxyphenyl)-1-methylethylamine as pale yellow oil; the purity: 96.1%.

$^1$H-NMR: 1.15 (d,3H), 2.65 (dd,1H), 2.78 (dd,1H), 3.81 (s,3H), 3.85 (s,3H), 4.29 (m,1H), 5.52 (bs,1H), 6.55–6.82 (m,3H), 8.06 (s,1H)

EXAMPLE 15

In the same manner as in Example 14 except that 134.5 g of 4'-methoxybenzyl methyl ketone was used in place of 3',4'-dimethoxybenzyl methyl ketone, the reaction and post treatment were carried out to obtain 142.6 g of crude N-formyl-2-(4-methoxyphenyl)-1-methylethylamine; the purity: 91.0%.

COMPARATIVE EXAMPLE 1

In the same manner as in Example 1 except that a mixture of formic acid, ammonium formate and acetophenone was heated with stirring at 160° C. for 6 hours in place of the concurrent addition of acetophenone and formic acid to ammonium formate for 3 hours and keeping the mass after the addition stirred for 3 hours, the reaction and post treatment were carried out to obtain 112 g of crude N-formyl-1-phenylethylamine; the purity: 82.7%.

COMPARATIVE EXAMPLE 2

In the same manner as in Example 4 except that a mixture of formic acid, ammonium formate and 2',4'-dichloroacetophenone was heated with stirring at 160° C. for 6 hours in place of the concurrent addition of 2',4'-dichloroacetophenone and formic acid to ammonium formate for 3 hours and keeping the mass ater the addition stirred for 3 hours, the-reaction and post treatment were carried out to obtain 178.6 g of crude N-formyl-1-(2,4-dichlorophenyl)ethylamine; the purity: 70.4%.

COMPARATIVE EXAMPLE 3

In the same manner as in Example 3 except that a mixture of formamide, formic acid and 4'-chloroacetophenone was heated with stirring at 160° C. for 6 hours in place of the concurrent addition of 4'-chloroacetophenone and formic acid to formamide for 3 hours and keeping the mass after the addition stirred for 3 hours, the reaction and post treatment were carried out to obtain 144.2 g of crude N-formyl-1-(4-chlorophenyl)ethylamine; the purity: 84.6%.

COMPARATIVE EXAMPLE 4

In the same manner as in Example 14 except that a mixture of formic acid, ammonium formate and 3',4'-dimethoxybenzyl methyl ketone was heated with stirring at 160° C. for 6 hours in place of the concurrent addition of 3',4'-dimethoxybenzyl methyl ketone and formic acid to ammonium formate for 3 hours and keeping the mass after the addition stirred for 3 hours , the reaction and post treatment were carried out to obtain 182.9 g of crude N-formyl-2-(3,4-dimethoxyphenyl)-l-methylethylamine; the purity: 60%.

EXAMPLE 16

162 g of crude N-formyl-1-(2,4-dichlorophenyl) ethylamine obtained in Example 5, 96 g of hot water at 80° C. and 121 g of 36% hydrochloric acid were mixed under stirring, and the mixture was refluxed for 1 hour.

Then, 224 g of water was added thereto while maintaining at a temperature of not lower than 70° C., and the mixture was extracted twice with 80 g of toluene at 70° C. 173 g of 48% aqueous sodium hydroxide solution was added to the aqueous layer, followed by extraction twice with 100 g of toluene at 60° C.

Then, the resulting toluene layers were combined, washed twice with 80 g of water, and the toluene was distilled off to obtain 128.8 g of crude 1-(2,4-dichlorophenyl)ethylamine; the purity: 93.4%.

118 g of purified 1-(2,4-dichlorophenyl)ethylamine was obtained by distillation under reduced pressure; the purity: 99.5%.

EXAMPLE 17

(1) Preparation of chloro-substituted phenyl alkyl ketoxime 122 g of hydroxylamine hydrochloride and 400 g of water were added to a mixture of 300 g of 2',40-dichloroacetophenone and 1200 g of methanol under stirring, heated to a temperature of 60° C., and the stirring was continued at the same temperature for 3 hours while a 27% aqueous sodium hydroxide solution was added thereto to adjust to pH 4 to 5.

Then, 27% aqueous sodium hydroxide solution was added thereto to adjust to pH 8, and 1200 g of water and methanol in total were distilled off under reduced pressure. 1200 g of water was added to the residue, followed by cooled to 25° C. The precipitated crystals were filtered, washed with 1200 g of water and dried to obtain 322 g of 2',4'-dichloroacetophenone oxide as white crystals (yield: 99%); the purity: 99.5%.

(2) Preparation of chloro-substituted phenyl alkyl ketoxime acetate 36.4 g of acetic anhydride was added to a mixture of 70 g of 2',4'-dichloroacetophenone oxime and 70 g of n-heptane, followed by stirring at 70° C. for 2 hours. A portion of the reaction mixture was taken out and analysis by gas chromatography showed that the raw material was disappeared.

The reaction mixture was cooled to 25° C., and the precipitated crystals were filtered to obtain 60.2 g of 2',4'-dichloroacetophenone oxime acetate as white needle crystals; the purity: 100%.

The filtrate was concentrated under reduced pressure, and the resulting residue (crystals) was washed with 10 g of ice-cooled n-heptane to obtain another 22.5 g of 2',4'-dichloroacetophenone oxime acetate as white needle crystals; the purity: 99%.

EXAMPLE 18

2 g (purity 100%) of 2',4'-dichloroacetophenone oxime acetate obtained in Example 17-(2), 20 g of acetic acid and 0.1 g of 5% platinum-carbon (50% water content) were placed in a 100 ml autoclave, the atmosphere was replaced with nitrogen, and the mixture were heated to 30° C., followed by pressurization with hydrogen to 20 kg/cm$^2$·G.

At the same temperature, the reaction was carried out for 5 hours while maintaining at pressure of 20 kg/cm$^2$·G by feeding hydrogen.

After the reaction, the catalyst was filtered, acetic acid in the filtrate was distilled off. 5 g of toluene was added to the residue, followed by washing with 18 g of a 5% aqueous sodium hydroxide solution and removal of the solvent in the organic layer, to obtain 1.54 g of oil, which was analyzed by gas chromatography.

Content of the oil:
1-(2',4'-dichlorophenyl)ethylamine; 94.5%,
N-1-(2,,4'-dichlorophenyl)ethyl-α-(2'1,4'-dichlorophenyl)ethylamine; 0.97%,
N-acetyl-α(2',4'-dichlorophenyl)ethylamide; 0.56%,
2',4'-dichloroacetophenone; 1%,
a dechlorinated compound; below the detection limit,
an alcohol obtained by reduction of carbonyl group; below the detection limit

EXAMPLE 19

In the same manner as in Example 18 except that 2 g of 4'-chloroacetophenone oxime acetate was used in place of 2',4'-dichloroacetophenone oxime acetate, the reaction and post treatment were carried out to obtain 1.47 g of oil.

Content of the oil
1-(4'-chlorophenyl)ethylamine; 98.8%,
N-acetyl-α-(4'-chlorophenyl)ethylamide; 0.91%,
a dechlorinated compound; not detected,
an alcohol obtained by reduction of carbonyl group; not detected.

EXAMPLE 20

In the same manner as in Example 18 except that 2 g of 3',4'-dichloroacetophenone oxime acetate was used in place of 2',4'-dichloroacetophenone oxime acetate, the reaction and post treatment were carried out to obtain 1.53 g of oil.

Content of the oil
1-(3',4'-dichlorophenyl)ethylamine; 89.8%,
1-(4'-chlorophenyl)ethylamine; 1.4%,
N-1-(3',4'-dichlorophenyl)ethyl-α-(3',4'-dichlorophenyl)ethylamine; 2.9%,
N-acetyl-α-(3',4'-dichlorophenyl)ethylamide; 1.9%,
an alcohol obtained by reduction of carbonyl group; not detected.

EXAMPLE 21

In the same manner as in Example 18 except that 2 g of 3',5'-dichloroacetophenone oxime acetate was used in place of 2',4'-dichloroacetophenone oxime acetate afforded 1.54 g of oil.

Content of the oil
1-(3',5'-dichlorophenyl)ethylamine; 88.7%,
1-(3'-chlorophenyl)ethylamine; 2%,
N-1-(3',5'-dichlorophenyl)ethyl-α-(3',5'-dichlorophenyl)ethyl amine; 2.9%,
N-acetyl-α-(3',5'-dichlorophenyl)ethylamide; 2.9%,
an alcohol obtained by reduction of carbonyl group; not detected.

EXAMPLE 22

36.4 g of acetic anhydride was added to a mixture of 70 g of 2',4'-dichloroacetophenone oxime and 210 g of acetic acid, followed by stirring at 100° C. for 2 hours. A portion of the reaction mixture was taken out and analysis by gas chromatography showed that a raw material was disappeared.

The whole amount of the above reaction mixture, 210 g of acetic acid, 3.9 g of 5% platinum-carbon (50% water content) were placed in a 1000 ml autoclave, the atmosphere was replaced with nitrogen, and the mixture were heated to 30° C., followed by pressurization with hydrogen to 20 kg/cm$^2$·G. At the same temperature, the reaction was carried out for 10 hours while maintaining at pressure of 20 kg/cm$^2$·G by feeding hydrogen.

After the reaction, the catalyst was filtered, acetic acid in the filtrate was distilled off. 100 g of toluene was added to the residue, followed by washing with 180 g of a 5% aqueous sodium hydroxide solution and removal of the solvent in the organic layer, to obtain 65 g of oil, which was analyzed by gas chromatography.

Content of the oil
1-(2',4'-dichlorophenyl)ethylamine; 91%,
1-(4'-chlorophenyl)ethylamine 2.9%,
N-1-(2',4'-dichlorophenyl)ethyl-α-(2',4'-dichlorophenyl)ethylamine; 1.1%,
N-acetyl-α-(2',4'-dichlorophenyl)ethylamide; 1.5%,
an alcohol obtained by reduction of carbonyl group; not detected.

58.5 g of 1-(2',4'-dichlorophenyl)ethylamine was obtained by distillation; the purity: 99%, boiling point: 130–132° C./20 mmHg.

EXAMPLE 23

The same manner as in Example 22 except that 0.57 g of 5% platinum-carbon (50% water content) and the whole catalyst recovered in Example 22 were used, the reaction and post treatment were carried out to obtain 64 g of oil.

Content of the oil
1-(2',4'-dichlorophenyl)ethylamine; 89.9%,
1-(4'-chlorophenyl)ethylamine; 1.8%,
N-1-(2',4'-dichlorophenyl)ethyl-α-(2',4'-dichlorophenyl)ethylamine; 3.4%,
N-acetyl-α-(2',4'-dichlorophenyl)ethylamide; 1.6%,
an alcohol obtained by reduction of carbonyl group; not detected.

EXAMPLE 24

In the same manner as in Example 18 except that the reaction was carried out while maintaining at the pressure of 5 kg/cm$^2$·G, the reaction and post treatment were carried out to obtain 1.52 g of oil.

Content of the oil
1-(2',4'-dichlorophenyl)ethylamine; 78.2%,
1-(4'-chlorophenyl)ethylamine; 4.6%,
N-1-(2',4'-dichlorophenyl)ethyl-α-(2',4'-dichlorophenyl)ethylamine; 6.1%, N-acetyl-α-(2',4'-dichlorophenyl)ethylamide; 1.9%,
2',4'-dichloroacetophenone; 0.4%,
an alcohol obtained by reduction of carbonyl group; not detected.

EXAMPLE 25

In the same manner as in Example 18 except that the reaction was carried out while maintaining at the pressure of 10 kg/cm$^2$·G, the reaction and post treatment were carried Out to obtain 1.54 g of oil.

Content of the oil
1-(2',4'-dichlorophenyl)ethylamine; 87.2%,
1-(4'-chlorophenyl)ethylamine; 3.7%, N-1-(2',4'-dichlorophenyl)ethyl-α-(2',4'-dichlorophenyl) ethylamine; 1.1%, N-acetyl-α-(2',4'-dichlorophenyl)ethylamide; 0.5%, 2',4'-dichloroacetophenone was 1.3%, an alcohol obtained by reduction of carbonyl group; not detected.

COMPARATIVE EXAMPLE 5

In the same manner as in Example 18 except that 0.1 g of 5% palladium-carbon (50% water content) was used in place of platinum-carbon and the reaction was carried out for 5 hours while maintaining at the pressure of 10 kg/cm²·G, the reaction and post treatment were carried out to obtain 1.49 g of oil.

Content of the oil 1-(2',4'-dichlorophenyl)ethylamine; 53.8%, phenylethylamine; 3.1%, 1-(4'-chlorophenyl)ethylamine; 16.9%, 1-(2'-chlorophenyl)ethylamine; 13.1%, N-1-(2',4'-dichlorophenyl)ethyl-α-(2',4'-dichlorophenyl) ethylamine; 6.2%, N-acetyl-α-(2',4'-dichlorophenyl) ethylamide; 4.7%, 2',4'-dichloroacetophenone was 0.5%.

COMPARATIVE EXAMPLE 6

In the same manner as in Example 22 except that 40.6 g of acetic anhydride was used, and the reaction was carried out while maintaining at the pressure of 10 kg/cm²·G, the reaction and post treatment were carried out to obtain 68 g of oil.

Content of the oil 1-(2',4'-dichlorophenyl)ethylamine; 51%, 1-(4'-chlorophenyl)ethylamine; 1%, N-1-(2',4'-dichlorophenyl)ethyl-α-(2',4'-dichlorophenyl) ethylamine 1.3%, N-acetyl-α-(2',4'-dichlorophenyl)ethylamide; 42.1%, 2',4'-dichloroacetophenone; 0.5%.

COMPARATIVE EXAMPLE 7

In the same manner as in Example 18 except that 20 g of methanol was used as a solvent, and the reaction was carried out while maintaining at the pressure of 10 kg/cm²·G, the reaction and post treatment were carried out to obtain 1.52 g of oil.

Content of the oil 1-(2',4'-dichlorophenyl)ethylamine; 12%,

N-1-(2',4'-dichlorophenyl)ethyl-α-(2',4'-dichlorophenyl) ethylamine; 63%,

N-acetyl-α-(2',4'-dichlorophenyl)ethylamide; 15%.

COMPARATIVE EXAMPLE 8

18.9 g of 2',4'-dichloroacetophenone, 35 g of methanol, 0.15 g of bis-(2-hydroxyethyl)sulfide, 0.1 g of ammonium acetate and 1.0 g of Raney-nickel catalyst (50% content) were placed in a autoclave, the atmosphere was replaced with nitrogen, and 4.6 g of liquid ammonia was added, followed by pressurization with hydrogen to 50 kg/cm²·G.

Then, the mixture was heated to 130° C., and the pressure was raised at 80 kg/cm²·G by feeding hydrogen, followed by reacting at the same temperature for 4 hours while maintaining at the pressure of 80 kg/cm²·G by feeding hydrogen.

After the reaction, the catalyst was filtered, and low boiling point fraction in the filtrate was distilled off under reduced pressure to obtain 19.5 g of oil, which was analyzed by gas chromatography.

Content of the oil 1-(2',4'-dichlorophenyl)ethylamine; 24.8 g, 1-(4'-chlorophenyl)ethylamine; 53.4%, unknown ingredients; 15.9%.

EXAMPLE 26

(1) A solution consisting of 16 g of (RS)-1-(2,4-dichlorophenyl)ethylamine and 10 ml of ethanol was heated to 70° C. while stirring, a solution consisting 12.8 g of L-mandelic acid and 40 ml of ethanol was added thereto over 30 minutes, and a temperature was raised to 75° C., followed by stirring at the same temperature for 30 minutes.

After cooling to 20° C. over 5 hours, the precipitated crystals were filtered and dried to obtain 13.2 g of diastereomer salt. 10 g of a 20% aqueous sodium hydroxide solution was added to the crystals, followed by extraction twice with 20 ml of toluene. The resulting organic layer was dried over magnesium sulfate, and the solvent was distilled off to obtain 7.3 g of (R)-1-(2,4-dichlorophenyl)ethylamine. This had the optical purity of 82%ee.

(2) The low boiling point fraction was distilled off from the mother liqourd from which the diastereomer has been filtered, to obtain 15.6 g of the residue. to this was added 13 g of a 20% aqueous sodium hydroxide solution, followed by extraction twice with 30 ml of toluene. The resulting toluene layer was dried over magnesium sulfate, and the solvent was distilled off to obtain 12.7 g of (S)-1-(2,4-dichlorophenyl) ethylamine. This had the optical purity of 70%ee.

(3) The remaining aqueous layers extracted in (1) and (2) were mixed, and 36% hydrochloric acid was added thereto to adjust to pH 0.7. Then, the mixture was extracted three times with 50 ml of ethyl acetate, dried over magnesium sulfate and the solvent was distilled off to obtain 12.3 g of L-mandelic acid.

EXAMPLE 7

(1) A solution consisting of 41 g of (RS)-1-(3,4-dichlorophenyl)ethylamine and 78 g of methyl t-butyl ether was heated to 45° C. while stirring, and a mixture of 14.6 g of L-mandelic acid and 90 g of methyl t-butyl ether was added thereto over about 30 minutes, followed by stirring at the same temperature for 30 minutes. Then, after cooled to 20° C. over 6 hours, the precipitated crystals were filtered, washed twice with 40 g of methyl t-butyl ether and dried to obtain 32.9 g of diastereomer salt. 82 g of a 5% aqueous sodium hydroxide solution was added to the crystals, followed by extraction twice with 20 g of methyl t-butyl ether. The solvent was distilled off from the resulting organic layer to obtain 18.2 g of (R)-1-(3,4-dichlorophenyl)ethylamine. This had the optical purity of 87.4%ee.

(2) The mother liquor from which the diastereomer salt has been filtered and the wash were combined, and 16 g of a 5% aqueous sodium hydroxide solution was added thereto for washing. The solvent was distilled off from the resulting organic layer to obtain 22.8 q of (S)-1-(3,4-dichlorophenyl) ethylamine. This had the optical purity of 70.2%ee.

EXAMPLE 28

(1) A solution consisting of 10 g of (RS)-1-(2,3-dichlorophenyl)ethylamine and 30 g of methyl t-butyl ether was heated to 45° C. while stirring, and a mixture of 3.6 g of L-mandelic acid and 30 g of methyl t-butyl ether was added thereto over about 30 minutes, followed by stirring at the same temperature for 30 minutes. Then, after cooled to 20° C. over 6 hours, the precipitated crystals were filtered, washed twice with 20 g of methyl t-butyl ether and dried to obtain 7.2 g of diastereomer salt. 21 g of a 5% aqueous sodium hydroxide solution was added to the crystals, followed by extraction twice with 10 g of methyl t-butyl ether. The solvent was distilled off from the resulting organic layer to obtain 4 g of (R)-1-(2,3-dichlorophenyl)ethylamine. This had the optical purity of 90.4%ee.

(2) The mother liquor from which the diastereomer salt has been filtered and the wash were combined, and 2 g of a 5% aqueous sodium hydroxide solution was added thereto for washing. The solvent was distilled off from the resulting organic layer to obtain 6 g of (S)-1-(2,3-dichlorophenyl)ethylamine. This had the optical purity of 58.8%ee.

EXAMPLE 29

(1) 0.28 g of zinc chloride was added to a mixture consisting of 62 g of (S)-1-(2',4'-dichlorophenyl)ethylamine (optical isomer ratio S/R=80.3/19.7) obtained in the same manner as in Example 26, 62 g of 2',4'-dichloroacetophenone and 130 g of toluene, followed by refluxing for 20 hours while the produced water was removed from the reaction system.

Then, the reaction mixture was washed with 10 g of a 5% aqueous sodium hydroxide solution at 25° C., and the layers were phase-separated. The resulting toluene layer was azeotropically dehydrated.

A portion thereof was taken out and analyzed by gas chromatography. As the result, it was calculated that the amount of N-($\alpha$-methyl-2',4'-dichlorobenzylidene)-$\alpha$-(2',4'-dic hlorophenyl)ethylamine contained in the toluene layer was 116 g, that of unreacted 1-(2',4'-dichlorophenyl)ethylamine was 1 g and that of 2',4'-dichloroacetophenone was 0.5 g.

(2) Then, at 30° C., a solution consisting of 1.2 g of potassium t-butoxide and 10.1 g of dimethyl sulfoxide was added to the toluene solution from which the moisture has been removed in the above step (1), and the mixture was stirred at the same temperature for 10 hours, followed by washing once with 233 g of a 10% sodium chloride solution and twice with 233 g of saturated sodium chloride solution.

(3) 285 g of 5% hydrochloric acid was added to the resulting toluene solution, and the mixture was stirred at 60° C. for 1 hour, followed by phase-separation of layers at the same temperature for 30 minutes by settling to obtain aqueous and toluene layers.

194 g of toluene was added to the aqueous layer to extract at 60° C., the resulting toluene layer and the above toluene layer were combined, and the solvent was distilled off to obtain 60.7 g of 2',4'-dichloroacetophenone.

72 g of a 27% aqueous sodium hydroxide solution was added to the aqueous layer extracted with toluene, the aqueous layer was extracted with 580 g of toluene, and the toluene was distilled off to obtain 61.7 g of 1-(2',4'-dichlorophenyl)ethylamine.

A portion of the latter was taken out and analyzed by high performance liquid chromatography with the optically active column. Optical isomer ratio was S/R=52.3/47.7.

EXAMPLE 30

In the same manner as in Example 29 except that (R)-1-(2',4'-dichlorophenyl)ethylamine (optical isomer ratio S/R=1/99) was used in place of (S)-1-(2',4'-dichlorophenyl)ethylamine, the reaction and post treatment were carried out to obtain 59.7 g of 2',4'-dichloroacetophenone and 61 g of 1-(2',4'-dichlorophenyl)ethylamine.

The latter had the optical isomer ratio of S/R=45.1/54.9

EXAMPLE 31

In the same manner as in Example 29-(1), a toluene solution containing 116g of optically active N-($\alpha$-methyl-2',4'-dichlorobenzylidene)-$\alpha$-(2',4'-dichlorophenyl) ethylamine was obtained.

Then, toluene and unreacted raw material were distilled off to obtain 111 g of optically active N-($\alpha$-methyl-2',4'-dichlorobenzylidene)-$\alpha$-(2',4'-dichlorophenyl)ethylamine as white crystals. E/Z=8/92, m.p.: 77–85° C. 1H-NMR: 1.32 (2d,3H), 1.51 (d,3H), 2.23 (s,3H), 2.29 (2s,3H), 4.56 (m,1H), 5.18 (m,1H), 6.6–7.8.(m,12H)

EXAMPLE 32

The reaction was carried out in the same manner as in Example 29-(2) except that a solution containing 111 g of optically active N-($\alpha$-methyl-2',4'-dichlorobenzylidene)-$\alpha$-(2',4'-dichlorophenyl)ethylamine and 130 g of dry toluene was used as a toluene solution.

Then, the resulting toluene solution was concentrated under reduced pressure, and the low boiling point fraction was distilled off at 100° C. at 20 mmug for 5 hours to obtain 110 g of racemic N-($\alpha$-methyl-2',4'-dichlorobenzylidene)-$\alpha$-(2',4'-dichlorophenyl)ethylamine as colorless oil. E/Z=8/92

EXAMPLE 33

In the same manner as in Example 29-(3) except that a solution containing 110 g of oil obtained in Example 32 and 130 g of toluene was used as a toluene solution, the reaction and post treatment were carried out to obtain 56.9 g of 2',4'-dichloroacetophenone and 57.8 g of 1-(2',4'-dichlorophenyl)ethylamine.

The latter had optical isomer ratio of S/R=51.9/48.1.

EXAMPLE 34

In the same manner as in Example 29 except that 0.45 g of titanium tetraisopropoxide was used in place of zinc chloride, the reaction and post treatment were carried out to obtain 59.2 g of 2',4'-dichloroacetophenone and 60.8 g of 1-(2',4'-dichlorophenyl)ethylamine.

The latter had the optical isomer ratio of S/R=53.3/46.7.

EXAMPLE 35

In the same manner as in Example 29 except that 0.62 g of p-toluenesulfonic acid was used in place of zinc chloride and xylene was used in place of toluene, the reaction and post treatment were carried out to obtain 59.1 g of 2',4'-dichloroacetophenone and 60.1 g of 1-(2',4'-dichlorophenyl)ethylamine.

The latter had the optical isomer ratio of S/R=53/47.

COMPARATIVE EXAMPLE 9

In the same manner as in Example 29 except that 20 g of t-butanol was used in place of dimethyl sulfoxide, the reaction and post treatment were carried out to obtain 60.3 g of 2',4'-dichloroacetophenone and 61.5 g of 1-(2',4'-dichlorophenyl)ethylamine. The latter had optical isomer ratio of S/R=80.3/19.7.

COMPARATIVE EXAMPLE 10

1.8 g of potassium t-butoxide was added to a mixture consisting of 6 g of (S)-1-(2',4'-dichlorophenyl)thylamine used in Example 29 and 9 g of dimethyl sulfoxide at 80° C., followed by stirring at the same temperature for 10 hours.

After cooled to room temperature, a portion thereof was taken out and optical isomer ratio was analyzed by high performance liquid column chromatography with optically active column.

Optical isomer ratio was S/R=80.3/19.7

EXAMPLE 36

0.05 g of zinc chloride was added to a mixture consisting of 5 g of (R)-1-(2'-chlorophenyl)ethylamine (optical isomer ratio S/R=24.8/75.2), 5 g of 2'-chloroacetophenone and 30 g of toluene, followed by reflux for 17 hours while the produced water was removed from the reaction system.

Then, in the same manner as in Example 31, the reaction and post treatment were carried out to obtain 8.9 g of optically active N-(α-methyl-2'-chlorobenzylidene)-α-(2'-chlorophenyl)ethylamine as pale yellow oil. E/Z=37/63

1H-NMR: 1.35 (2d,3H), 1.57 (d, 3H), 2.22 (s,3H), 2.31 (2s,3H), 4.65 (2m,1H), 5.2 (m,1H), 6.6–7.9 (m,8H)

EXAMPLE 37

10 g of toluene was added to 8 g of the oil obtained in Example 36. A solution consisting of 0.6 g of potassium t-butoxide and 6.8 g of dimethyl sulfoxide was added thereto at 30° C., the mixture was stirred at the same temperature for 23 hours and washed once with 20 g of a 10% sodium chloride solution and twice with 20 g of a saturated sodium chloride solution. The resulting toluene layer was concentrated under reduced pressure, and the low boiling point fraction was distilled off at 100° C. and 20 mmlg for 5 hours to obtain 7.9 g of racemic N-(α-methyl-2'-chlorobenzylidene)-α-(2'-dichloro phenyl)ethylamine as pale yellow oil. E/Z=37/63

EXAMPLE 38

10 g of toluene and 25 g of 5% hydrochloric acid were added to 7.9 g of the oil obtained in Example 37. The mixture was stirred at 60° C. for 1 hour and was phase-separated at the same temperature for 30 minutes to obtain the aqueous layer and the toluene layer. 17 g of toluene was added to the aqueous layer, followed by extraction at 60° C. The resulting toluene layer and the above toluene layer were combined, and the solvent was distilled off to obtain 4.1 g of 2'-chloroacetophenone.

6.4 g of a 27% aqueous sodium hydroxide solution was added to the aqueous layer after extracted with toluene, the aqueous solution was extracted with 50 g of toluene, and the toluene was distilled off to obtain 4.1 g of 1-(2'-chlorophenyl)ethylamine.

A portion of the latter was taken out and analyzed by high performance liquid column chromatography using the optically active column.

Optical isomer ratio was S/R=40.4/59.6.

EXAMPLE 39

0.05 g of zinc chloride was added to a mixture consisting of 5 g of (R)-1-(3',4'-dichlorophenyl)ethylamine (optical isomer ratio S/R=6.3/93.7) obtained in the same manner as in Example 27, 5 g of 3',4'-dichloroacetophenone and 30 g of toluene, followed by reflux for 27 hours while the produced water was removed from the reaction system.

Then, in the same manner as in Example 31, the reaction and post treatment were carried out to obtain 9 g of optically active N-(α-methyl-3',4'-dichlorobenzylidene)-α-(3',4'-dichlorophenyl)ethylamine as pale yellow oil. E/Z=94/6

1H-NMR: 1.35 (2d,3H), 1.47 (d,3H), 2.23 (s,3H), 2.31 (s,3H), 4.15 (m,1H), 4.77 (m,1 H), 7.25–8.0 (m,6H)

EXAMPLE 40

10 g of toluene was added to 8 g of the oil obtained in Example 39. A solution consisting of 0.25 g of potassium t-butoxide and 2.8 g of dimethyl sulfoxide was added thereto at 30° C., the mixture was stirred at the same temperature for 2 hours, and washed once with 20 g of 10% sodium chloride solution and twice with 20 g of saturated sodium chloride solution. The resulting toluene layer was concentrated under reduced pressure, and the low boiling point fraction was distilled off at 100° C. and 20 mmag for 5 hours to obtain 7.9 g of racemic N-(α-methyl-3',4'-dichlorobenzylidene)-α-(3', 4'-dichlorophenyl)ethylamine as pale yellow oil. E/Z=94/6

EXAMPLE 41

10 g of toluene and 25 g of 5% hydrochloric acid were added to 7.9 g of the oil obtained in Example 40. The mixture was stirred at 60° C. for 1 hour and phase-separated at the same temperature for 30 minutes to obtain the aqueous layer and the toluene layer.

17 g of toluene was added to the aqueous layer, followed by extraction at 60° C. The resulting toluene layer and the above toluene layer were combined, and the solvent was distilled off to obtain 4 g of 3',4'-dichloroacetophenone.

6.4 g of a 27% aqueous sodium hydroxide solution was added to the aqueous layer after extracted with toluene, the aqueous solution was extracted with 50 g of toluene, and the toluene was distilled off to obtain 4 g of 1-(3',4'-dichlorophenyl)ethylamine.

A portion of the latter was taken out and analyzed by high performance liquid column chromatography using the optically active column. The optical isomer ratio was S/R=49.2/50.8.

EXAMPLE 42

0.05 g of zinc chloride was added to a mixture consisting of 5 g of (R)-1-(4'-chlorophenyl)ethylamine (optical isomer ratio S/R=20.0/80.0), 5 g of 4'chloroacetophenone and 30 g of toluene, followed by reflux for 25 hours while the produced water was removed from the reaction system.

Then, in the same manner as in Example 31, the reaction and post treatment were carried out to obtain 9 g of optically active N-(α-methyl-4'-chlorobenzylidene)-α-(4'-chlorophenyl)ethylamine as pale yellow oil. E/Z=93/7

1H-NMR: 1.35 (d,3H), 1.47 (d,3H), 2.23 (s,3H), 2.30 (s,3H), 4.32 (m,1H), 4.78 (m,1H), 6.95–7.8 (m,8H)

EXAMPLE 43

10 g of toluene was added to 8 g of the oil obtained in Example 42. A solution consisting of 0.21 g of potassium t-butoxide and 2.4 g of dimethyl sulfoxide was added thereto at 30° C., the mixture was stirred at the same temperature for 2 hours, and washed once with 20 g of 10% sodium chloride solution and twice with 20 g of saturated sodium chloride solution. The resulting toluene layer was concentrated under reduced pressure, and the low boiling point fraction was distilled off at 100° C. and 20 mmHg for 5 hours to obtain 7.9 g of racemic N-(α-methyl-4'-chlorobenzylidene)-α-(4'-chlorophenyl)ethylamine as pale yellow oil. E/Z=93/7

EXAMPLE 44

10 g of toluene and 25 g of 5% hydrochloric acid were added to 7.9 g of the oil obtained in Example 43. The mixture was stirred at 60° C. for 1 hour and phase-separated at the same temperature for 30 minutes to obtain the aqueous layer and the toluene layer.

17 g of toluene was added to the aqueous layer, followed by extraction at 60° C. The resulting toluene layer and the above toluene layer were combined, and the solvent was distilled off to obtain 4 g of 4'-chloroacetophenone.

6.4 g of a 27% aqueous sodium hydroxide solution was added to the aqueous layer afer extracted with toluene, the aqueous solution was extracted with 50 g of toluene, and the toluene was distilled off to obtain 4 g of 1-(4'-chlorophenyl)ethylamine.

A portion of the latter was taken out and analyzed by high performance liquid column chromatography using the optically active column. The optical isomer ratio was S/R=48.5/51.5

COMPARATIVE EXAMPLE 11

0.6 g of potassium t-butoxide was added to a mixture of 2 g of (R)-1-(2'-chlorophenyl)ethylamine used in Example 36 and 10 g of dimethyl sulfoxide at 80° C., and the mixture was continued to stir at the same temperature for 6 hours.

Then, 10 g of toluene was added thereto, and the reaction mixture was washed twice with 10 g of saturated sodium chloride solution, dried over anhydrous sodium sulfate, and the toluene was distilled off to obtain 2.1 g of brown oil. Purification by distillation afforded 1.58 g of 1-(2'-chlorophenyl)ethylamine. A portion thereof was taken out and optical isomer ratio was analyzed by high performance liquid chromatography with the.optically active column. The optical isomer ratio S/R=28.4/71.6

COMPARATIVE EXAMPLE 12

0.6 g of potassium t-butoxide was added to a mixture of 2 g of (R)-1-(3',4'-dichlorophenyl)ethylamine used in Example 39 and 6 g of dimethyl sulfoxide at 80° C., and the mixture was continued to stir at the same temperature for 6 hours.

Thene 10 g of toluene was added thereto, and the reaction mixture was washed twice with 10 g of-saturated sodium chloride solution, dried over anhydrous sodium sulfate, and the toluene was distilled off to obtain 2.1 g of brown oil. Purification by distillation afforded.0.6 g of 1-(3',4'-dichlorophenyl)ethylamine. A portion thereof was taken out and optical isomer ratio was analyzed by high performance liquid chromatography with the optically active column. The optical isomer ratio S/R=22.9/77.1

COMPARATIVE EXAMPLE 13

0.24 g of potassium t-butoxide was added to a mixture of 2 g of (R)-1-(4'-chlorophenyl)ethylamine used in Example 42 and 4 g of dimethyl sulfoxide at 80° C., and the mixture was continued to stir at the same temperature for 4 hours.

Then, 10 g of toluene was added thereto, and the reaction mixture was washed twice with 10 g of saturated sodium chloride solution, dried over anhydrous sodium sulfate, and the toluene was distilled off to obtain 2.1 g of brown oil. Purification by distillation afforded 1.66 g of 1-(4'-chlorophenyl)ethylamine. A portion thereof was taken out and optical isomer ratio was analyzed by high performance liquid chromatography with the optically active column. The optical isomer ratio S/R=48.5/51.5

EXAMPLE 45

0.045 g of zinc chloride was added to a mixture consisting of 5 g of (S)-1-(3'-methoxyphenyl)ethylamine (optical isomer ratio S/R=72.0/28.0), 5 g of 3'-methoxyacetophenone and 30 q of toluene, followed by reflux for 10 hours while the produced water was removed from the reaction system.

Then, in the same manner as in Example 31, the reaction and post treatment were carried out to obtain 8.7 g of optically active N-(α-methyl-3e-methoxybenzylidene)-α-(3'-methoxyphenyl)ethylamine as pale yellow oil. E/Z=78/22

1HNR: 1.38 (2d,3H), 1.53 (d,3H), 2.25 (s,3H), 2.31 (2s,3H), 3.79 (s,3H), 3.82 (s,3H), 4.09 (m,1H), 4.79 (m,1H), 6.5–7.5 (2m,8H)

EXAMPLE 46

10 g of dry toluene was added to 8 g of the oil obtained in Example 45. 1.58 g of potassium t-butoxide and 14.4 g of dizmethyl sulfoxide was added thereto at 30° C., the mixture was stirred at the same temperature for 6.5 hours, and washed once with 20 g of 10% sodium chloride solution and twice with 20 g of saturated sodium chloride solution.

The resulting toluene layer was concentrated under reduced pressure, and the low boiling point fraction was distilled off at 100° C. and 20 mmHg for 5 hours to obtain 7.9 g of racemic N-(α-methyl-3'-methoxybenzylidene)-α-(3'-methoxyphenyl)ethylamine as pale yellow oil. E/Z=78/22

EXAMPLE 47

10 g of toluene and 25 g of 5% hydrochloric acid were added to 7.9 g of the oil obtained in Example 46. The mixture was stirred at 60° C. for 1 hour and phase-separated at the same temperature for 30 minutes to obtain the aqueous layer and the toluene layer.

17 g of toluene was added to the aqueous layer, followed by extraction at 60° C. The resulting toluene layer and the above toluene layer were combined, and the solvent was distilled off to obtain 4.1 g of 3'-methoxyacetophenone.

6.4 g of a 27% aqueous sodium hydroxide solution was added to the aqueous layer after extracted with toluene, the aqueous solution was extracted with 50 g of toluene, and the toluene was distilled off to obtain 4.1 g of 1-(3'-methoxyphenyl)ethylamine.

A portion of the latter was taken out and analyzed by high performance liquid column chromatography using the optically active column.

Optical isomer ratio was S/R=54.0/46.0

EXAMPLE 48

The condensation reaction was carried out in the same manner as in Example 45 except that 5 g of (S)-1-(3',4'-dimethoxyphenyl)ethylamine (optical isomer ratio S/R= 80.6/19.4) was used in place of 5 g of (S)-1-(3'-methoxyphenyl)ethylamine, 5 g of 3',4'-dimethoxyacetophenone was used in place of 5 g of 3'-methoxyacetophenone and reflux was continued for 12 hours in place of 10 hours.

Then, in the same manner as in Example 31, the reaction and post treatment were carried out to obtain 8.9 g of optically active N-(α-methyl-3',4'-dimethoxybenzylidene)-α-(3 4'-dimethoxyphenyl)ethylamine as pale yellow crystals. E/Z=76/24

1H-NMR: 1.28 (2d,3H), 1.44 (d,3H), 2.20 (s,3H), 2.28 (2s,3H), 3.79 (s,3H), 3.83 (s,3H), 3.89 (2s, 3H), 4.03 (m,1H), 4.72 (m,1), 6.7–7.5 (2m,6H)

EXAMPLE 49

7.9 g of racemic N-(α-methyl-3',4'-dimethoxybenzylidene )-α-(3',4'- dimethoxyphenyl) ethylamine as pale yellow oil was obtained according to the same manner as that in Example 46 except that 8 g of the crystals obtained in Example 48 was used in place of 8 g of the oil obtained in Example 45, potassium t-butoxide was used at an amount of 1.31 g in place of 1.58 gt dimethyl sulfoxide was used at an amount of 11.9 g in place of 14.4 g and stirring was continued for 4 hours in place of 6.5 hours. E/Z=76/24

EXAMPLE 50

In the same manner as in Example 47 except that 7.9 g of the oil obtained in Example 49 was used in place of 7.9 g of the oil obtained in Example 46, the reaction and post reatment were carried out to obtain 4 g of 3',4'-dimethoxyacetophenone and 4 g of 1-(3',4'-dimethoxyphenyl)ethylamine. The latter had optical isomer ratio of S/R=55.5/44.5.

EXAMPLE 51

The condensation reaction was performed in the same manner as in Example 45 except that 5 g of (R)-1-(2'-fluorophenyl)ethylamine (optical isomer ratio S/R13.6/86.4) was used in place of 5 g of (S)-1-(3'-methoxyphenyl) ethylamine, 5 g of 2'-fluaroacetophenone was used in place of 5 g of 3'-methoxyacetophenone, zinc chloride was used at an amount of 0.05 g in place of 0.045 g, and reflux was continued for 5.5 hours in place of 10 hours.

Then, in the same manner as in Example 31, the reaction and post treatmet were carried out to obtain 8.7 g of optically active N-(α-methyl-2'-fluorobenzylidene)-α-(2'-fluorophenyl)ethylamine as pale yellow oil. E/Z=66/34

1H-NMR: 1.39 (2d,3H), 1.56 (d,3H), 2.28 (d,3H), 2.33 (s,3H), 4.63 (m,1H), 5.17 (m,1H), 6.9–7.7 (2m,8H)

EXAMPLE 52

7.9 g of racemic N-(α-methyl-2'-fluorobenzylidene)-α-(2'-fluorophenyl)ethylamine was obtained as pale yellow oil in the same manner as in Example 46 except that 8 g of the oil obtained in Example 51 was used in place of 8 g of the oil obtained in Example 45, potassium t-butoxide was used at an amount of 0.69 g in place of 1.58 g, dimethyl oulfoxide was used at an amount of 6.3 g in place of 14.4 g, and stirring was continued for 1 hour in place of 6.5 hours. E/Z=66/34

EXAMPLE 53

In the same manner as in Example 47 except that 7.9 g of the oil obtained in Example 52 was used in place of 7.9 g of the oil obtained in Example 46, the reaction and post treatment were carried out to obtain 4.1 g of 2'-fluoroacetophenone and 4.1 g of 1-(2'-fluorophenyl) ethylamine. The latter had optical isomer ratio of S/R=49.3/50.7

COMPARATIVE EXAMPLE 44

1.34 g of potassium t-butoxide and 6.8 g of dimethyl sulfoxide were added to 2 g of (S)-1-(3'-methoxyphenyl) ethylamine (optical isomer ratio S/R=72.0/28.0), followed by stirring at 30° C. for 16 hours. After 10 g of toluene was added tereto, the mixture was washed twice with 10 g of saturated aqueous sodium chloride solution, dried over anhydrous sodium sulfate and the solvent was distilled off to obtain 2.1 g of brown oil. Purification by distillation afforded 1.9 g of 1-(3'-methoxyphenyl)ethylamine. Optical isomer ratio was S/R=72.0/28.0.

COMPARATIVE EXAMPLE 15

2.1 g of brown oil was obtained in the same manner as in Comparative Example 14 except that 2 g of (S)-1-(3',4'-dimethoxyphenyl)ethylamine (optical isomer ratio S/R= 80–6/19.4) was used in place of 2 g of (S)-1-(3'-methoxyphenyl)ethylamine, potassium t-butoxide was used at an amount of 0.62 g in place of 1.34 g, dimethyl sulfoxide was used at an amount of 5.7 g in place of 6.8 g, and stirring was continued for 6 hours in place of 16 hours. Purification by distillation afforded 1.9 g of 1-(3',4'-dimethoxyphenyl) ethylamine. Optical isomer ratio was S/R=80.6/19.4.

COMPARATIVE EXAMPLE 16

2.1 g of brown oil was obtained in the same manner as in Comparative Example 14 except that 2 g of (R)-1-(2'-fluorophenyl)ethylamine (optical isomer ratio S/R=13.6/86.4) was used in place of 2 g of (S)-1-(3'-methoxyphenyl) ethylamine, potassium t-butoxide was used at an amount of 0.38 g in place of 1.34 g, dimethyl sulfoxide was used at an amount of 3.5 g in place of 6.8 g, and stirring was continued for 5 hours in place of 16 hours. Purification by distillation afforded 1.9 g of 1-(2'-fluorophenyl)ethylamine. Optical isomer ratio was S/R=13.6/86.4.

COMPARATIVE EXAMPLE 17

The reaction was performed in the same manner as in Example 46 except that 15 g of tert-butanol was used in place of dimethyl sulfoxide, and the reaction and post treatment was carried out in the same manner as in Example 47 to obtain 4.1 g of 3'-methoxyacetophenone and 4.1 g of 1-(3'-methoxyphenyl)ethylamine. The latter had optical isomer ratio of S/R=72.0/28.0

What is claimed is:

1. A process for producing a racemate of an N-(α-alkylbenzylidene)-α-phenylalkylamine represented by formula (1):

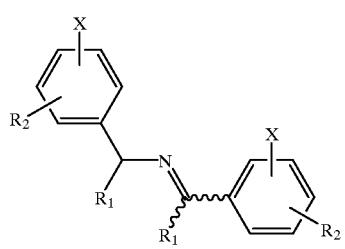

(1)

wherein the $R^1$, substituents may be the same or different and represent a lower alkyl group, the $R^2$ substituents may be the same or different and represent a hydrogen atom, a halogen atom, a lower alkyl group or a lower alkoxy group, and the X substituents may be the same or different and represent a halogen atom or a lower alkoxy group, which comprises treating an optically active isomer of anl N-(α-alkylbenzylidene)-α-phenylalkylamine (1) with an alkali metal alkoxide in the presence of dimethyl sulfoxide.

2. The process according to claim 1, wherein the treatment is carried out at a temperature of not higher than 50° C.

3. The process according to claim 2, wherein the optically active isomer of the N-(α-alkylbenzylidene)-α-phenylalkylamnine (1) is obtained by condensing an optically active isomer of an α-phenylalkylamine represented by formula (2):

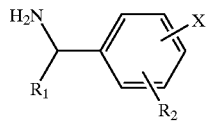

(2)

wherein $R^1$, $R^2$ and X are as defined above, with a phenyl alkyl ketone represented by formula (3):

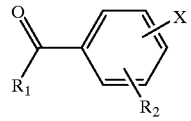

(3)

wherein $R^1$, $R^2$ and X are as defined above.

4. The process according to claim 3, wherein the condensation is carried out in the presence of at least one selected from the group consisting of a Lewis acid, a sulfonic acid and a heteropolyacid.

5. The process according to claim 3, wherein the optically active isomer of the α-phenylalkylamine (2) is obtained by concurrently adding a phenyl alkyl ketone (3) and formic acid to formamide and/or ammonium formate to obtain an N-formylamine represented by formula (4):

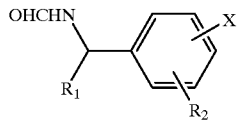

(4)

wherein $R^1$, $R^2$ and X are as defined above, hydrolyzing the N-formylamine (4) to obtain a racemate of an α-phenylalkylamine (2), and then optically resolving the thus obtained racemate.

6. The process according to claim 3, wherein the optically active isomer of the α-phenylalkylamine (2) is obtained by catalytic hydrogenation of oxime acetate represented by formula (5):

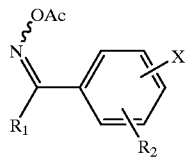

(5)

wherein $R^1$, $R^2$ and X are as defined above, in a carboxylic acid in the presence of a platinum catalyst to obtain a racemate of an α-phenylalkylamine (2), and then optically resolving the thus obtained racemate.

7. The process according to claim 6, wherein the oxime acetate (5) is obtained by reacting ketoxime represented by formula (6):

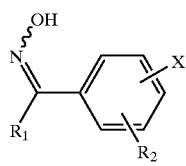

(6)

wherein $R^1$, $R^2$ and X are as defined above, with an acylating agent.

8. The process according to claim 7, wherein the ketoxime (6) is obtained by reacting a phenyl alkyl ketone (3) with a salt of hydroxylamine and an acid.

9. The process according to claim 1, wherein 0.01 to 2 moles of the alkali metal alkoxide are used per 1 mole of N-(α-alkylbenzylidene)-α-phenylalkylamine.

10. The process according to claim 1, wherein 0.1 to 10 moles of dimethyl sulfoxide are used per 1 mole of N-(α-alkylbenzylidene)-α-phenylalkylamine.

11. The process according to claim 1, wherein the process is carried out in the presence of a solvent.

12. The process according to claim 11, wherein the solvent is selected from the group consisting of aromatic hydrocarbons, ethers, aliphatic hydrocarbons and dimethyl sulfoxide.

* * * * *